United States Patent
Dammalapati et al.

(10) Patent No.: US 11,897,913 B2
(45) Date of Patent: Feb. 13, 2024

(54) SYNTHESIS OF 3'-DEOXYADENOSINE-5'-O-[PHENYL (BENZYLOXY-L-ALANINYL)]PHOSPHATE (NUC-738)

(71) Applicant: NuCana plc, Edinburgh (GB)

(72) Inventors: Venkata Lakshmi Narasimha Rao Dammalapati, Hyderabad (IN); Mani Bushan Kotala, Hyderabad (IN)

(73) Assignee: NuCana plc, Edinburgh (GB)

( * ) Notice: Subject to any disclaimer, the term of this patent is extended or adjusted under 35 U.S.C. 154(b) by 0 days.

(21) Appl. No.: 16/623,272

(22) PCT Filed: Jun. 14, 2018

(86) PCT No.: PCT/GB2018/051641
§ 371 (c)(1),
(2) Date: Dec. 16, 2019

(87) PCT Pub. No.: WO2018/229495
PCT Pub. Date: Dec. 20, 2018

(65) Prior Publication Data
US 2020/0181190 A1    Jun. 11, 2020

(30) Foreign Application Priority Data
Jun. 14, 2017    (GB) .................................... 1709471

(51) Int. Cl.
| C07H 19/207 | (2006.01) |
| C07H 1/02 | (2006.01) |
| C07H 19/10 | (2006.01) |
| C07H 19/20 | (2006.01) |

(52) U.S. Cl.
CPC .............. *C07H 19/207* (2013.01); *C07H 1/02* (2013.01); *C07H 19/10* (2013.01); *C07H 19/20* (2013.01)

(58) Field of Classification Search
CPC ........ C07H 19/207; C07H 1/02; C07H 19/10; C07H 19/20
See application file for complete search history.

(56) References Cited

U.S. PATENT DOCUMENTS

| 4,357,324 | A | 11/1982 | Montgomery et al. |
| 8,263,575 | B2 | 9/2012 | McGuigan et al. |
| 8,871,737 | B2 | 10/2014 | Smith et al. |
| 9,090,642 | B2 | 7/2015 | Cho et al. |
| 10,149,859 | B2 | 12/2018 | Liotta et al. |
| 10,538,541 | B2 | 1/2020 | Yuan et al. |
| 10,570,168 | B2 | 2/2020 | Griffith et al. |
| 10,689,413 | B2 | 6/2020 | Yuan et al. |
| 10,774,104 | B2 * | 9/2020 | Kotala .................... C07F 9/222 |
| 10,906,929 | B2 | 2/2021 | Griffith et al. |
| 2009/0206007 | A1 | 12/2009 | Wagner |
| 2012/0070411 | A1 | 3/2012 | Beigelman |
| 2017/0253629 | A1 | 9/2017 | Griffith et al. |
| 2018/0237466 | A1 | 8/2018 | Yuan et al. |
| 2018/0244701 | A1 | 8/2018 | Yuan et al. |
| 2018/0369266 | A1 | 12/2018 | Kennovin et al. |
| 2019/0374564 | A1 | 12/2019 | Griffith et al. |
| 2019/0375778 | A1 | 12/2019 | Griffith et al. |
| 2020/0181189 | A1 | 6/2020 | Griffith et al. |
| 2020/0181190 | A1 | 6/2020 | Dammalapati et al. |
| 2021/0130387 | A1 | 5/2021 | Griffith et al. |
| 2022/0031727 | A1 | 2/2022 | Griffith et al. |

FOREIGN PATENT DOCUMENTS

| CN | 105646629 A | 6/2016 |
| WO | WO 2005/012327 A2 | 2/2005 |
| WO | WO 2006/063149 A1 | 6/2006 |
| WO | WO 2006/10043 9 A1 | 9/2006 |
| WO | WO 2010/108140 A1 | 9/2010 |
| WO | WO 2012/040126 A1 | 3/2012 |
| WO | WO 2012/040127 A1 | 3/2012 |
| WO | WO 2015/081133 A2 | 6/2015 |
| WO | WO-2016/083830 A1 | 6/2016 |
| WO | WO 2016/145142 A1 | 9/2016 |
| WO | WO 2016/181093 A1 | 11/2016 |
| WO | WO 2017/207986 A1 | 12/2017 |
| WO | WO 2017/207989 A1 | 12/2017 |
| WO | WO 2018/229495 A1 | 12/2018 |

OTHER PUBLICATIONS

Aman et al., "From Adenosine to 3'-Deoxyadenosine: Development and Scale Up," Org Proc Res Dev 4(6):601-605 (2000).
Bazin et al., "A Convenient Preparation of 3'-Deoxyadenosine (Cordycepin) and 9-[3'(R)-Deuterio-β-D-2'(R)-pentofuranosyl]-adenine," Synthesis 12:1108-1111 (1985).
International Search Report and Written Opinion for International Application No. PCT/GB2018/051641 dated Nov. 10, 2018.
Ross et al., "Synthesis of Diastereomerically Pure Nucleotide Phosphoramidates," J Org Chem 76(20):8311-8319 (2011).
Blanka Gönczy; "Design, Synthesis and Biological Evaluation of Nucleotide Pro-drugs Centred on Clinically Active Anticancer Nucleosides," Thesis of Cardiff School of Pharmacy and Pharmaceutical Sciences Cardiff University; 2016.
Congiatu, Costantino; et al., "Design, Synthesis and Biological Evaluation of Some Novel Nucleotide Prodrugs as Potential Anticancer Agents," A Thesis submitted to the University of Wales for the Degree of Philosophiae Doctor, 2006; p. 1-290.
Kim, Sung Eun; et al.; "Deoxyribosyl analogues of nethionyl and isoleucyl sulfamate adenylates as inhibitors of methionyl-tRNA and isoleucyl-tRNA synethtases," Elsevier; Bioorganic & Medicinal Chemistry Letters 15 (2005) 3388-3393.
Nyilas, A., et al.; "The Cordycepin Analogue of 2,5A and its Threo Isomer. Chemical Synthesis, Conformation and Biological Activity," Department of Bioorganic Chemistry, UK, Acta Chemica Scandinavica B00 (1986); pp. 68-688.

(Continued)

*Primary Examiner* — Layla D Berry
(74) *Attorney, Agent, or Firm* — Knowles Intellectual Property Strategies, LLC

(57) ABSTRACT

The present invention generally relates to a novel process for the preparation of 3'-deoxyadenosine derivatives, and particularly NUC-7738 (3'-deoxyadenosine-5'-O-[phenyl(benzyloxy-L-alaninyl)] phosphate) an anticancer ProTide of deoxyadenosine.

8 Claims, No Drawings

(56) References Cited

OTHER PUBLICATIONS

Nyilas, A'gnes and Jyoti Chattopadhyaya; "A Convenient Preparation of 9-(3'-Deoxy-β-D-threo-pentofuranosyl)-adenine and 9-[3'Deoxy-3'-(S)-deuterio-β-D-2'-(s)-pentofuranosyl]-adenine," Synthesis, Department of Bioorganic Chemistry, Biomedical Center, Box 581, Uppsala University, S-751 23 Uppsala, Sweden, 1986; pp. 196-198.

Robins, Morris J.; et al.; "A Mild Conversion of Vicinal Diols to Alkenes, Efficient Transformation of Ribonucleosides into 2'-Ene and 2'3'-Dideoxynucleosides," Tetrahedron Letters, vol. 25, No. 4, pp. 367-370, Pergamon Press Ltd.; 1984.

Zeng, Debin; et al.; "Discovery of 2'-α-C-Methyl-2'-β-C-fluorouridine Phosphoramidate Prodrugs as Inhibitors of Hepatitis C Virus," ACS Medicinal Chemistry Letters; DOI: 10.1021/acsmedchemlett.6b00270 ACS Med. Chem. Lett. 2016, 7, 1197-1201.

Antunez, Carmen Jimenez, "Design, Synthesis and Biological Evaluation of Nucleoside Phosphoramidates with potential Anticancer Activity," A thesis submitted for the degree of Philosophiae Doctor in Cardiff University Jan. 2017.

Cho, J. H. et al.; "Efficient synthesis of Exo-N-carbamoyl Nucleosides: application to the synthesis of phosphoramidate prodrugs," Organic Letters, 14(10):2488-2491, 2012.

Cho, J.H. et al.; "Efficient synthesis of nucleoside aryloxy phosphoramidate prodrugs utilizing benzylocarbonyl protection," Tetrahedron, 67(30):5487-5493, 2011.

Ferrari, Valentina, "Synthesis and Biological Evaluation of Novel Nucleosides and Nucleotides as Potential Therapeutic Agents," Thesis Cardiff University, Sep. 2015.

Filippov et al. "Synthesis of the antibiotically active part of agrocin 84," Tetrahedron Letters, 39:4891-4894 (1998).

Jones et al. "Synthesis and anti-HIV activity of some Novel Phosphorodiamidate Derivatives of 3'-azido-3'-deoxythymidine (AZT)" Antiviral Chemistry & Chemotherapy (1991) 2(1) pp. 35-39.

McGuigan et al., "Design, synthesis and evaluation of a novel double pro-drug: INX-08189. A new clinical candidate for hepatitis C virus," Bioorg. Med. Chem. Lett. 2010, 20 pp. 4850-4854.

McGuigan et al., "Phosphoramidate derivatives of AZT as inhibitors of HIV: studies on the carboxyl terminus," Antiviral Chemistry & Chemotherapy, 1993; 4(2):97-101.

Murziani, Paola; "Anticancer Drug Design and Synthesis" Thesis submitted to the Welsh School of Pharmacy, Cardiff University; Jul. 18, 2016.

Thomsen, Liv Sondergaard; "Synthesis, biological evaluation, and mechanistic investigations of potential anticancer nucleotide phosphoramidates" Thesis submitted to Cardiff University; May 2011 (Publicly available Aug. 30, 2013).

Van de Vijver et al., "Antibacterial 5'-(B-dipeptidyl)-sulfamoyladenosines," Bioorganic and Medicinal Chemistry, 17: 260-269 (2009).

Wagner et al., "Pronucleotides: Toward the In Vivo Delivery of Antiviral and Anticancer Nucleotides," Med. Res. Rev. 20, No. 6, pp. 417-451, 2000.

U.S. Pat. No. 10,570,168, B2, U.S. Appl. No. 15/518,527, Griffith et al., filed Feb. 25, 2020.

U.S. Pat. No. 8,263,575, B2, U.S. Appl. No. 11/886,931, McGuigan et al., filed Sep. 11, 2012.

U.S. Pat. No. 10,906,929, B2, U.S. Appl. No. 16/305,153, Griffith et al., filed Feb. 2, 2021.

US 2019/0375778, A1, U.S. Appl. No. 16/305,159, Griffith et al., filed Dec. 12, 2019.

US 2020/0181189, A1, U.S. Appl. No. 16/782,952, Griffith et al., filed Jun. 11, 2020.

US 2021/0130387, A1, U.S. Appl. No. 17/142,936, Griffith et al., filed Jun. 6, 2021.

* cited by examiner

SYNTHESIS OF 3'-DEOXYADENOSINE-5'-O-[PHENYL (BENZYLOXY-L-ALANINYL)]PHOSPHATE (NUC-738)

RELATED APPLICATIONS

This application is a § 371 national stage application based on Patent Cooperation Treaty Application serial number PCT/GB2018/051641, filed Jun. 14, 2018; which claims the benefit of priority to GB 1709471.5, filed Jun. 14, 2017.

FIELD OF THE INVENTION

The present invention generally relates to a novel process for the preparation of 3'-deoxyadenosine derivatives, and particularly NUC-7738 (3'-deoxyadenosine-5'-O-[phenyl (benzyloxy-L-alaninyl)] phosphate) an anticancer ProTide of deoxyadenosine.

BACKGROUND OF THE INVENTION

Cordycepin is 3'-deoxyadenosine (3'dA). It is a nucleoside analogue of adenosine that lacks the 3'-hydroxyl group on the ribose moiety.

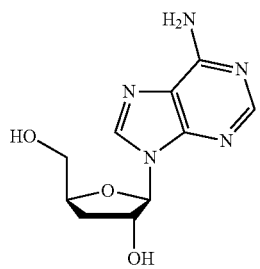

3'-deoxyadenosine (cordycepin, 3'dA)

Cordycepin has been studied most extensively as an anti-cancer agent but it has been found not to be particularly potent. NUC-7738 is a ProTide derivative of cordycepin that has shown excellent activity in vitro against a range of solid tumours, leukaemias and lymphomas (see WO2016/083830).

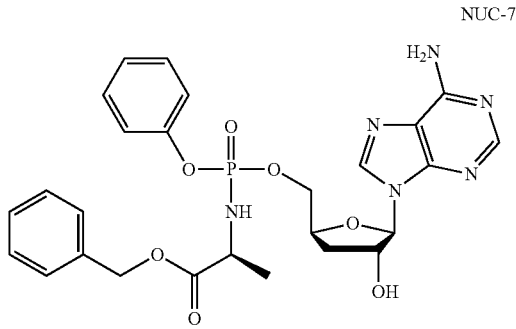

NUC-7738

It is an aim of certain embodiments of this invention to enable access to 2'-protected deoxyadenosine that can be converted into prodrugs of cordycepin and prodrugs of cordycepin phosphate nucleotides such as NUC-7738.

It is an aim of certain embodiments of this invention to provide a method of providing the cordycepin derivatives which is scalable, economic and/or efficient, e.g. more scalable, economic and/or efficient than known methods.

Another aim of certain embodiments of this invention is to provide a method which provides cordycepin derivatives in substantially pure form and at the same time meet or exceed the necessary criteria stipulated by organisations such as the US FDA concerning the amounts and nature of any trace impurities which arise from synthesis and separation.

Certain embodiments of this invention satisfy some or all of the above aims.

SUMMARY OF THE INVENTION

In accordance with a first aspect of the invention there is provided a process for the preparation of NUC-7738 (I)

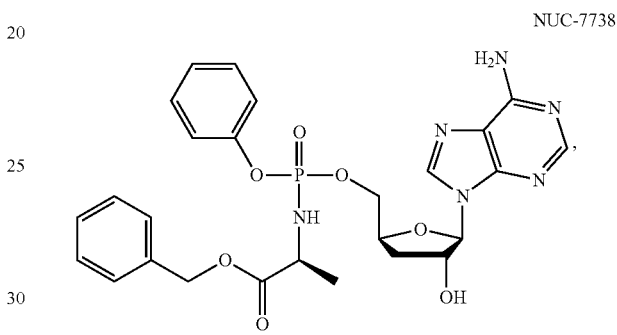

NUC-7738 the process comprising step d), e) and f):

d) removing the protecting group $P^1$ from a compound of formula (II) to provide 2'-protected cordycepin (I)

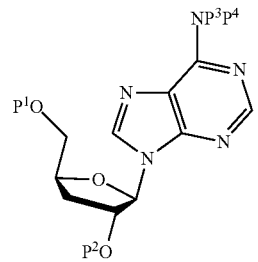

(II)

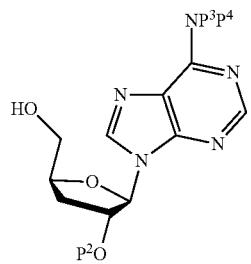

(I)

wherein $P^2$ is a protecting group and $P^3$ and $P^4$ are independently selected from H and a protecting group;

e) reacting the compound of formula (I) with a compound of formula (III), where LG is a leaving group, in the presence of a base (B1) to provide a compound of formula (IV)

(III)

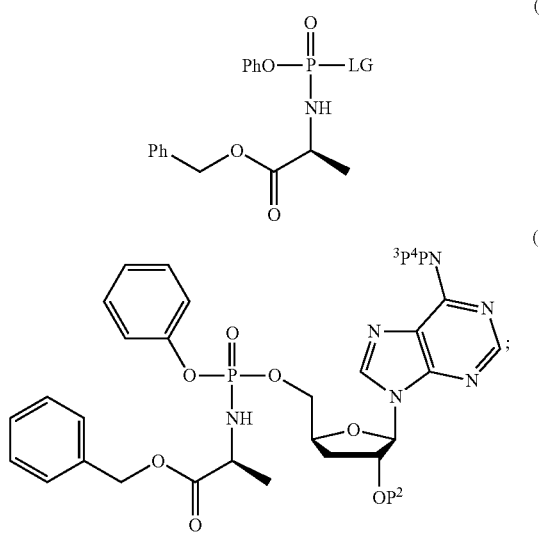
(IV)

f) removing protecting group P² and, where P³ and P⁴ are protecting groups, removing P³ and P⁴ to provide NUC-7738.

The process may comprise step c):

c) introducing the protecting group P² onto the 2' hydroxy group of a compound of formula (V) to provide a compound of formula (II).

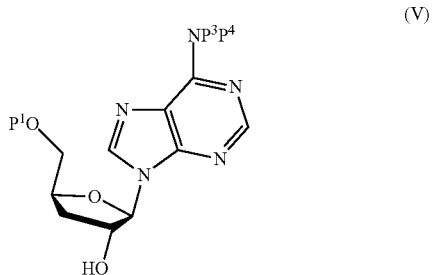
(V)

The process may comprise step b):

b) treating a compound of formula (VI) with a source of hydride to provide a compound of formula (V).

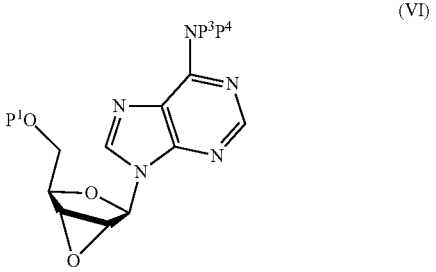
(VI)

The process may comprise step a):

a) introducing the protecting group P¹ onto the 5' hydroxy group of a compound of formula (VII) to provide a compound of formula (VI).

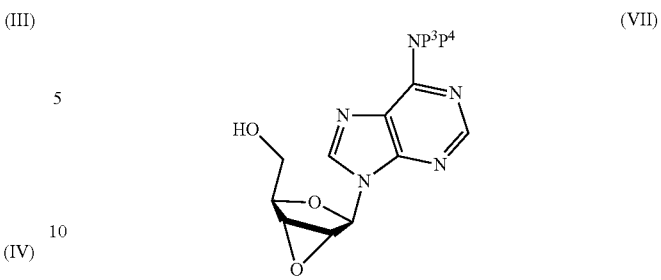
(VII)

A protecting group for a hydroxyl group (e.g. $P^1$ and $P^2$) may be independently selected from optionally substituted —Si($C_1$-$C_6$-alkyl)$_3$, optionally substituted —C(O)—$C_1$-$C_6$-alkyl, optionally substituted —C(O)-aryl, optionally substituted —C(O)—O$C_1$-$C_6$-alkyl, —C(O)—O-allyl, —C(O)—O—$CH_2$-fluorenyl, optionally substituted —C(aryl)$_3$, optionally substituted —($C_1$-$C_3$-alkylene)-aryl, optionally substituted —C(O)O$CH_2$-aryl and —$C_1$-$C_4$-alkyl-O—$C_1$-$C_4$-alkyl.

According to some embodiments, $P^1$ is independently selected from optionally substituted —Si($C_1$-$C_6$-alkyl)$_3$, optionally substituted —C(O)—$C_1$-$C_6$-alkyl, optionally substituted —C(O)-aryl, optionally substituted —C(O)—O$C_1$-$C_6$-alkyl, —C(O)—O-allyl, —C(O)—O—$CH_2$-fluorenyl, optionally substituted —C(aryl)$_3$, optionally substituted —($C_1$-$C_3$-alkylene)-aryl, optionally substituted —C(O)O$CH_2$-aryl and —$C_1$-$C_4$-alkyl-O—$C_1$-$C_4$-alkyl.

$P^1$ may be independently selected from optionally substituted —Si($C_1$-$C_6$-alkyl)$_3$, optionally substituted —C(O)—O$C_1$-$C_6$-alkyl and optionally substituted —C(O)O$CH_2$-aryl, —C(O)—O-allyl. Preferably, $P^1$ is selected from —C(O)O-tBu, —C(O)O-benzyl and —C(O)O$CH_2$-allyl. Thus, $P^1$ may be —C(O)O$CH_2$-aryl. $P^1$ may be —C(O)O-tBu.

Alternatively, $P^1$ may be independently selected from optionally substituted —C(O)—$C_1$-$C_6$-alkyl and optionally substituted —C(O)-aryl, e.g. $P^1$ may be independently selected from benzoyl and acetyl.

In a further alternative, $P^1$ may be optionally substituted —Si($C_1$-$C_6$-alkyl)$_3$. $P^1$ may be —Si($C_1$-$C_4$-alkyl)$_3$. The alkyl groups may be unsubstituted. $P^1$ may be t-butyldimethylsilyl.

According to some embodiments, $P^2$ is independently selected from optionally substituted —Si($C_1$-$C_6$-alkyl)$_3$, optionally substituted —C(O)—$C_1$-$C_6$-alkyl, optionally substituted —C(O)-aryl, optionally substituted —C(O)—O$C_1$-$C_6$-alkyl, —C(O)—O-allyl, —C(O)—O—$CH_2$-fluorenyl, optionally substituted —C(aryl)$_3$, optionally substituted —($C_1$-$C_3$-alkylene)-aryl, optionally substituted —C(O)O$CH_2$-aryl and —$C_1$-$C_4$-alkyl-O—$C_1$-$C_4$-alkyl.

$P^2$ may be independently selected from optionally substituted —Si($C_1$-$C_6$-allkyl)$_3$, optionally substituted —C(O)—O$C_1$-$C_6$-alkyl and optionally substituted —C(O)O$CH_2$-aryl, —C(O)—O-allyl. Preferably, $P^2$ is selected from —C(O)O-tBu, —C(O)O-benzyl and —C(O)O$CH_2$-allyl. Thus, $P^2$ may be —C(O)O$CH_2$-aryl. $P^2$ may be —C(O)O-tBu.

Alternatively, $P^2$ may be independently selected from optionally substituted —C(O)—$C_1$-$C_6$-alkyl and optionally substituted —C(O)-aryl, e.g. $P^2$ may be independently selected from benzoyl and acetyl.

In a further alternative, $P^2$ may be optionally substituted —Si($C_1$-$C_6$-alkyl)$_3$. $P^2$ may be —Si($C_1$-$C_4$-alkyl)$_3$. $P^2$ may be t-butyldimethylsilyl.

It may be that $P^1$ and $P^2$ are each optionally substituted —Si($C_1$-$C_6$-alkyl)$_3$. It may be that $P^1$ and $P^2$ are each optionally substituted —Si(C$_1$-C$_4$-alkyl)$_3$. The alkyl groups may be unsubstituted. It may be that P$^1$ and P$^2$ are each t-butyldimethylsilyl.

The inventors have found that protection of both the 2' and 5' with silyl protecting groups (e.g. TBDMS) provides the largest overall yield of NUC-7738. It might have been expected that an orthogonal protecting group strategy would be optimal but this has been found not to be the case. This is in part due to low yields for protection steps using other protecting groups. In particular, selective deprotection of the 5'-TBDMS using TFA has been shown to be very effective, providing a higher overall yield than approaches using orthogonal protecting groups with lower yields for protection steps, e.g. steps a) and c).

A protecting group for an amino group (e.g. P$^3$ and P$^4$) may at each occurrence be independently selected from —C(O)OC$_1$-C$_6$-alkyl, optionally substituted —C(O)OCH$_2$-aryl, —C(O)—O-allyl, —C(O)—O—CH$_2$-fluorenyl, optionally substituted —C(aryl)$_3$, optionally substituted —(C$_1$-C$_3$-alkylene)-aryl, optionally substituted —C(O)—C$_1$-C$_6$-alkyl, optionally substituted —C(O)-aryl, —S(O)$_2$-C$_1$-C$_6$-alkyl, optionally substituted —S(O)$_2$-aryl and optionally substituted —Si(C$_1$-C$_6$-alkyl)$_3$.

P$^3$ may be independently selected from —C(O)OC$_1$-C$_6$-alkyl, optionally substituted —C(O)OCH$_2$-aryl, —C(O)—O-allyl, —C(O)—O—CH$_2$-fluorenyl, optionally substituted —C(aryl)$_3$, optionally substituted —(C$_1$-C$_3$-alkylene)-aryl, optionally substituted —C(O)—C$_1$-C$_6$-alkyl, optionally substituted —C(O)-aryl, —S(O)$_2$-C$_1$-C$_6$-alkyl, optionally substituted —S(O)$_2$-aryl and optionally substituted —Si(C$_1$-C$_6$-alkyl)$_3$.

P$^3$ may be independently selected from —C(O)OC$_1$-C$_6$-alkyl, optionally substituted —C(O)OCH$_2$-aryl, —C(O)—O-allyl, optionally substituted —C(aryl)$_3$, and optionally substituted —Si(C$_1$-C$_6$-alkyl)$_3$. Preferably, P$^3$ is selected from —C(O)O-tBu, —(O)O-benzyl and —C(O)OCH$_2$-allyl. Thus, P$^3$ may be —C(O)OCH$_2$-aryl.

Alternatively, P$^3$ may be independently selected from optionally substituted —C(O)—C$_1$-C$_6$-alkyl and optionally substituted —C(O)-aryl, e.g. P$^3$ may be independently selected from benzoyl and acetyl.

In another alternative, P$^3$ is H.

P$^4$ may be independently selected from H, —C(O)OC$_1$-C$_6$-alkyl, optionally substituted —C(O)OCH$_2$-aryl, —C(O)—O-allyl, —C(O)—O—CH$_2$-fluorenyl, optionally substituted —C(aryl)$_3$, optionally substituted —(C$_1$-C$_3$-alkylene)-aryl, optionally substituted —C(O)—C$_1$-C$_6$-alkyl, optionally substituted —C(O)-aryl, —S(O)$_2$—C$_1$-C$_6$-alkyl, optionally substituted —S(O)$_2$-aryl and optionally substituted —Si(C$_1$-C$_6$-alkyl)$_3$.

Preferably, P$^4$ is H.

It may be that P$^3$ and P$^4$ are each H.

It may be that P$^3$ and P$^4$ are each H and P$^2$ is t-butyldimethylsilyl.

It may be that P$^3$ and P$^4$ are each H and P$^1$ and P$^2$ are each t-butyldimethylsilyl.

Step d)

Where P$^1$ is acid sensitive (e.g. trityl, C(O)OtBu, MOM, MEM, 2,4-dimethoxybenzyl, 2,3-dimethoxybenzyl, —C(Me)$_2$—) step d) can be conducted using a suitable acid. The acid may be a Bronsted acid (e.g. TsOH, TFA, phosphoric acid, HCl, or formic acid) or a Lewis acid (e.g. ZnBr$_2$, CeCl$_3$). Lewis acids (e.g. ZnBr$_2$) are less preferred. HCl is likewise less preferred. The acid may be TFA.

Where P$^1$ is a silyl group (e.g. triethylsilyl or t-butyldimethylsilyl, step d) can be conducted using a suitable acid (e.g. CAN, TsOH, TFA, AcOH, PTSA, PPTS, citric acid) or using a suitable fluorine source (e.g. tetrabutylammonium fluoride, fluorosilicic acid, HF). The acid may be TFA.

It may be that P$^1$ and P$^2$ are each silyl (e.g. TBDMS). In such occurrences TFA is a preferred reagent for selectively removing the 5' silyl protecting groups in the presence of the 2'silyl protecting group.

The reaction may be conducted in a mixture of acetonitrile and water. The reaction may be conducted in a mixture for which the acetonitrile:water ratio is in the range from 2:1 to 10:1. The reaction may be conducted in a mixture for which the acetonitrile:water ratio is in the range from 3:1 to 6:1. The reaction may be conducted at a temperature that is in the range from 0 to 20° C.

Compounds of Formula II may be synthesized from the parent nucleoside (cordycepin) by protecting the hydroxy and optionally the amino groups with suitable protecting groups. Protecting groups (e.g. P$^1$, P$^2$, P$^3$ and/or P$^4$) can typically be added and removed using conventional protecting group methodology, for example, as described in "Protective Groups in Organic Chemistry," edited by J W F McOmie (1973); "Protective Groups in Organic Synthesis," 2$^{nd}$ edition, T W Greene (1991); and "Protecting Groups", 3$^{rd}$ addition P. J Koscienski (1995).

It may be necessary to prepare the compounds of formula II by first protecting the 5'-hydroxy group of the parent nucleoside with a protecting group which is orthogonal to those which will be used to protect the 3' and/or 2'-hydroxy and/or amino group (i.e. a group which can be removed from the 5'-hydroxyl group without also removing the desired 2'-hydroxyl and/or amino protecting groups). Simultaneously or subsequently, the 2'-hydroxyl and/or amino groups are protected with the desired protecting group(s). Certain protecting groups (e.g. TBDMS) can be simultaneously introduced onto the 2'-hydroxyl and 5'-hydroxyl and then selectively removed from the 5' hydroxyl group without being removed from the 2'-hydroxyl.

Alternatively, the compounds of formula II can be prepared via one or more (or all) of steps a) to c) described herein.

Step e)

LG may be selected from halo, alkyl sulfonyl, aryl sulfonyl, heteroaryloxy or substituted phenoxy.

LG may be halo, e.g. chloro. The compound of formula (III) may be:

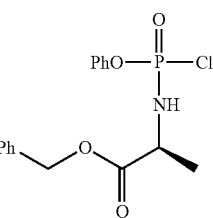

LG may be substituted phenoxy. The compound of formula (III) may be a compound of formula (VIII):

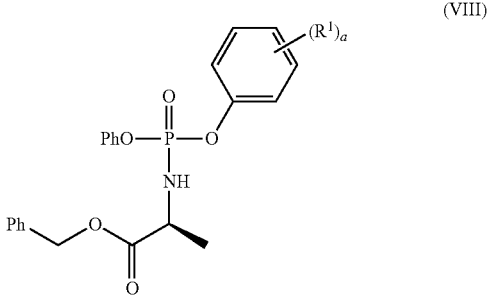

(VIII)

R¹ may be selected from the group comprising: halo group (e.g. selected from fluoro, bromo, chloro or iodo); trifluoromethyl, cyano and nitro. a is an integer between 1 and 5. R¹ may be at each occurrence halo, e.g. fluoro. a may be 5.

Where LG is phenoxy, displacement of the substituted phenoxy group takes place selectively with inversion of phosphate stereocentre.

ProTides can typically exist in two diastereoisomeric forms, epimeric at the phosphate centre. The two diastereoisomers of NUC-7738 are:

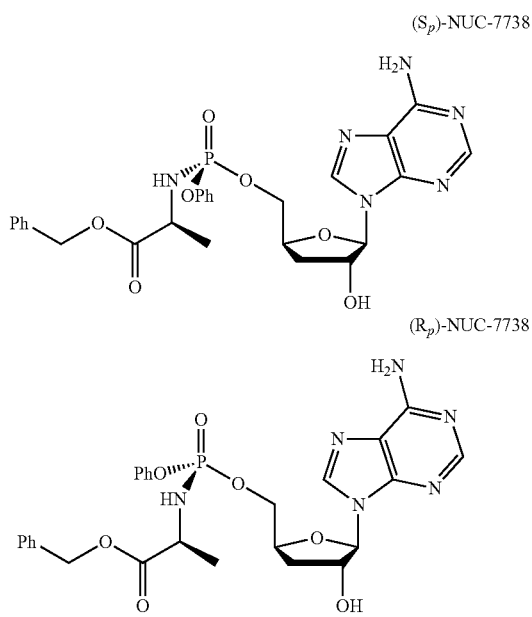

The ($S_p$)-diastereoisomer of the phenoxy precursor (i.e. the compound of formula (VIII)) provides the ($S_p$)-diastereoisomer of the ProTide and the ($R_p$)-diastereoisomer of the precursor provides the ($R_p$)-diastereoisomer of the ProTide.

Thus, it may be that the process is a method of making the NUC-7738 in diastereomerically enriched form and the compound of formula (VIII) is in diastereomerically enriched form.

It may be that the process is a method of making the ($R_p$)-diastereoisomer of NUC-7738 in diastereomerically enriched form and the compound of formula (VIII) is the ($R_p$)-diastereoisomer in diastereomerically enriched form.

It may be that the process is a method of making the ($S_p$)-diastereoisomer of NUC-7738 in diastereomerically enriched form and the compound of formula (VIII) is the ($S_p$)-diastereoisomer in diastereomerically enriched form.

Alternatively, it may be that the process is a method of making the NUC-7738 as a mixture of diastereoisomers and the compound of formula (III) (e.g. the compound of formula (VIII)) is a mixture of diastereoisomers.

The base (B1) might be a nitrogen base. Nitrogen bases include N-alkylimidazoles, (e.g. N-methyl imidazole (NMI)), imidazole, optionally substituted pyridines, (e.g. collidine, pyridine, 2,6-lutidine) and trialkylamines (e.g. triethylamine, and diisopropylethylamine). Alternatively, the base (B1) may be an organometallic base or metal hydride base (e.g. NaH). Thus, the base may be a Grignard reagent (i.e. an alkylmagnesium halide). Exemplary Grignard reagents include t-butylmagnesium halides such as tBuMgCl, tBuMgBr. Preferably, the base is tBuMgCl.

Step e) may be carried out in a solvent S1.

The process may comprise:
  g) suspending or dissolving the $R_p$-diastereoisomer of the compound of Formula (VIII) or a mixture of the ($R_p$)- and ($S_p$)-diastereoisomers of the compound of formula (VIII) in a solvent (S2),
  h) treating the solution or suspension with a base (B2) to obtain ($S_p$)-diastereoisomer of the compound of formula (VIII) in substantially diastereomerically enriched form, and
  i) isolating the ($S_p$)-diastereoisomer of formula (VIII).

The base (B2) may be selected from the group consisting of organic amine bases (e.g. primary, secondary, tertiary amines, cyclic amine; exemplary organic amine bases include bases include N-alkylimidazoles, [e.g. N-methyl imidazole (NMI), imidazole, optionally substituted pyridines, (e.g. collidine, pyridine, 2,6-lutidine) and trialkylamines (e.g. triethylamine, and diisopropylethylamine)]; or inorganic bases (e.g. alkali metal hydroxide, alkali metal carbonates, alkali metal alkoxides, alkali metal aryloxides). Preferably, B2 is a tertiary amine. Thus, B2 may be a trialkylamine. Most preferably, B2 is triethylamine.

The solvent S2 may be selected from the group consisting of amides, ethers, esters, ketones, aromatic hydrocarbons, halogenated solvents, nitriles, sulfoxides, sulfones and mixtures thereof. S2 may be an organic solvent. Organic solvents include but are not limited to ethers (e.g. tetrahydrofuran, dioxane, diethyl ether, t-butylmethylether); ketones (e.g. acetone and methyl isobutyl ketone); halogenated solvents (e.g. dichloromethane, chloroform and 1,2-dichloroethane); hydrocarbons (e.g. cyclohexane, pentane, hexane, heptane), aromatic solvents (e.g. benzene and toluene), esters (e.g. ethyl acetate) and amides (e.g. DMF, NMP); or mixtures thereof. Preferably, S2 is a hydrocarbon or is a mixture comprising a hydrocarbon. Where S2 is a mixture, it may be a mixture that comprises over 50% (e.g. over 70%) of the hydrocarbon. The hydrocarbon may be hexane. The hydrocarbon may be heptane. S2 may be a mixture of hexane or heptane and a polar organic solvent (e.g. an ether, ester, alcohol or halogenated solvent). S2 may be a mixture of hexane or heptane and a polar organic solvent, the mixture comprising over 50% (e.g. over 70%) by volume hexane or heptane. S2 may be a mixture of hexane or heptane and ethyl acetate. S2 may be a mixture of heptane and ethyl acetate. S2 may be a mixture of hexane or heptane and ethyl acetate, the mixture that comprising over 50% (e.g. over 70%) by volume hexane or heptane. S2 may be a mixture of heptane and ethyl acetate, the mixture comprising over 50% (e.g. over 70%) by volume heptane. S2 may be a mixture of hexane or heptane and methyl-t-butylether. S2 may be a mixture of hexane and methyl-t-butylether. S2 may be a mixture of hexane or heptane and methyl-t-butylether, the mixture that comprising over 50% (e.g. over 70%) by volume hexane or heptane. S2 may be a mixture of hexane and methyl-t-butylether, the mixture comprising over 50% (e.g. over 70%) by volume hexane.

Step h) may involve stirring the mixture of the compound of formula (VIII) and the base B2 for 2 h or longer. Step h) may involve stirring the mixture of the compound of formula (VIII) and the base B2 for 6 h or longer. Step h) may involve stirring the mixture of the compound of formula (VIII) and the base B2 for 10 h or longer. Step d) may involve stirring the mixture of the compound of formula (VIII) and the base B2 for 16 h or longer. Step h) may involve stirring the mixture of the compound of formula (VIII) and the base B2 for up to 36 h.

Step h) may involve stirring the mixture of the compound of formula (VIII) and the base B2 at a temperature from 0 to 50° C. Step h) may involve stirring the mixture of the compound of formula (VIII) and the base B2 at a temperature from 10 to 35° C.

In certain specific embodiments, the compound of Formula (VIII) is a compound selected from:

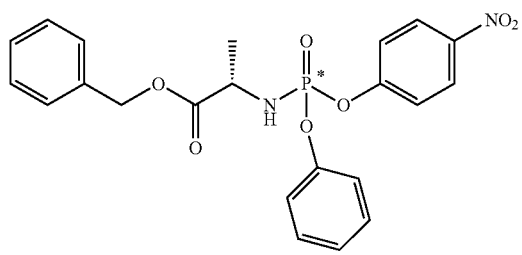

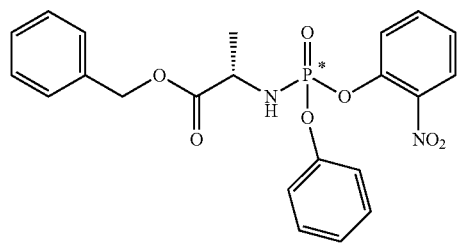

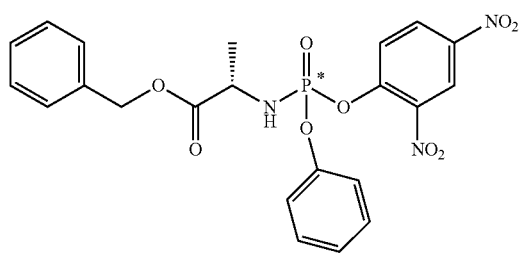

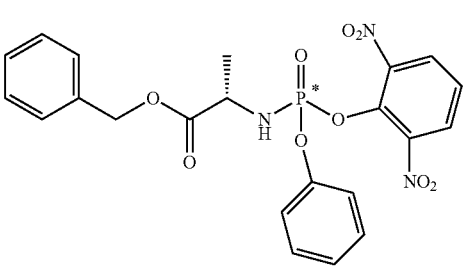

-continued

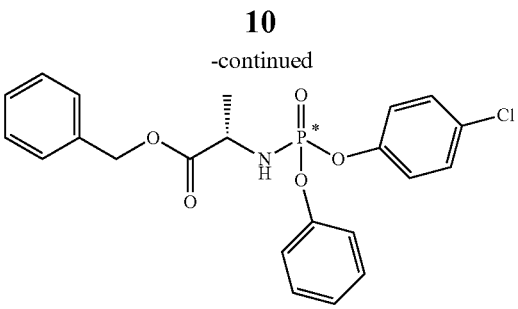

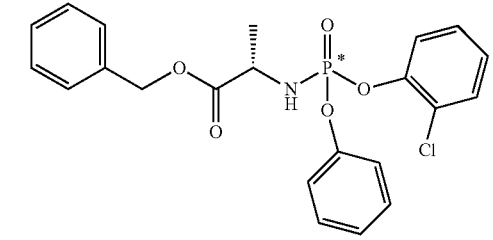

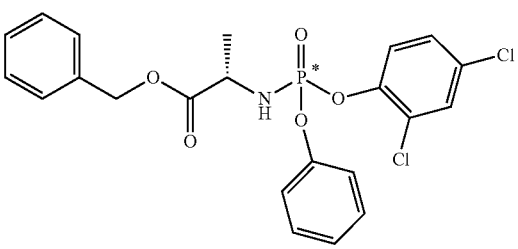

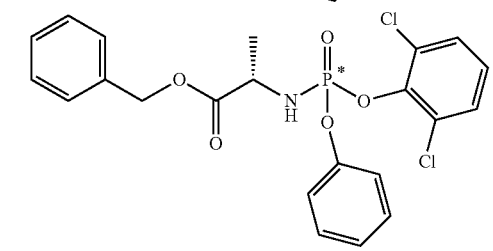

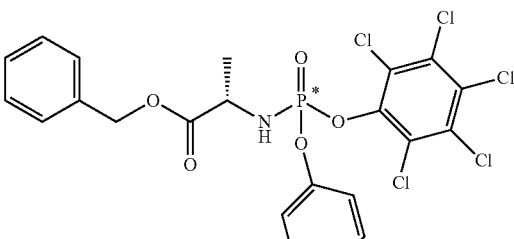

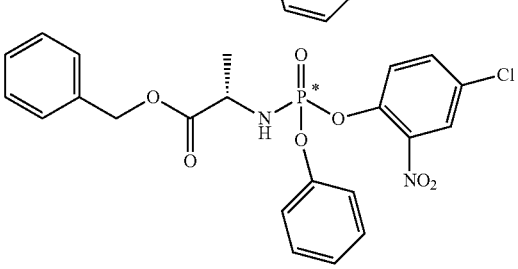

11
-continued
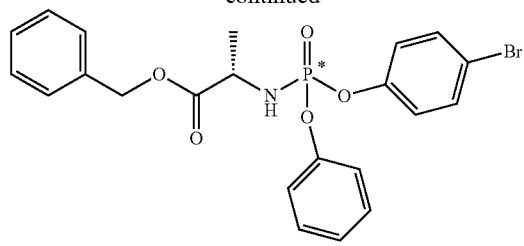
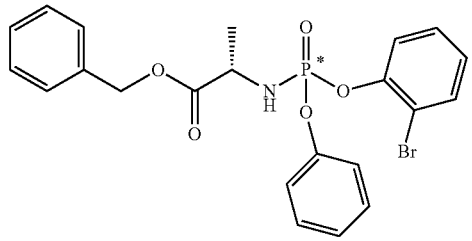
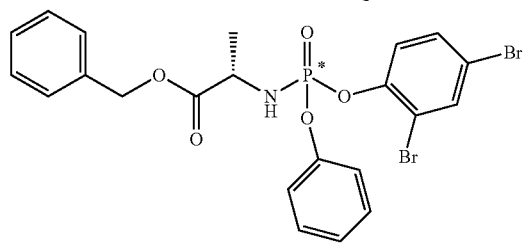
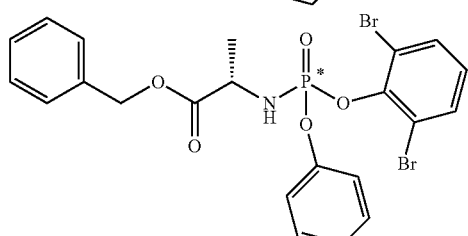
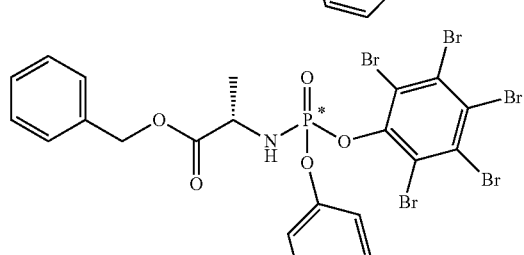
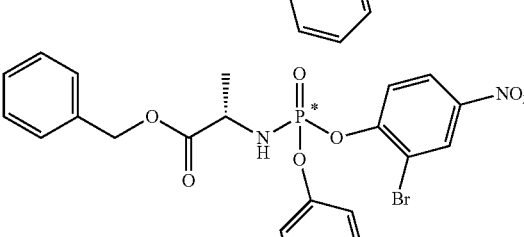
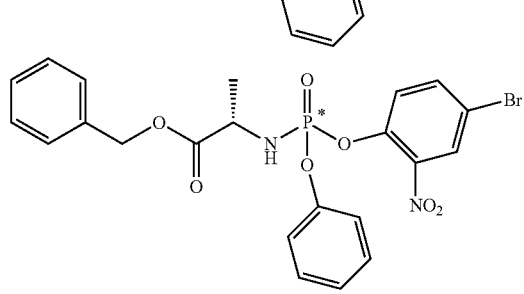
12
-continued
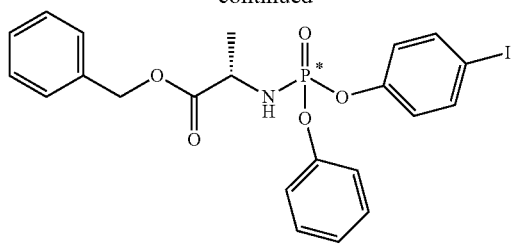
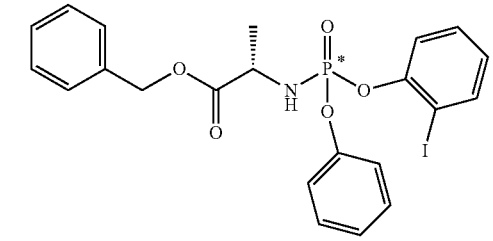
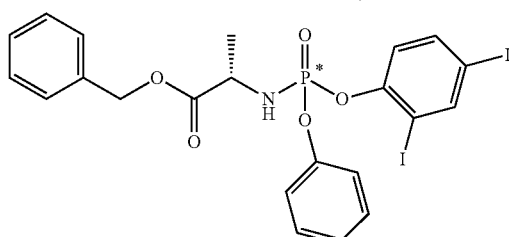
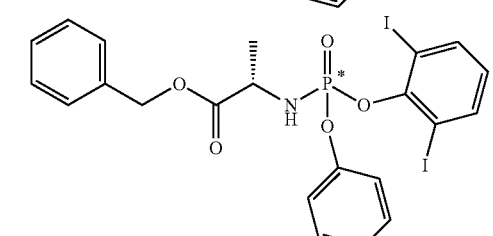
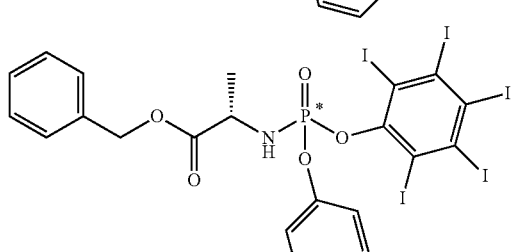
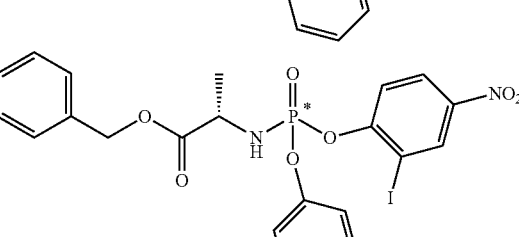
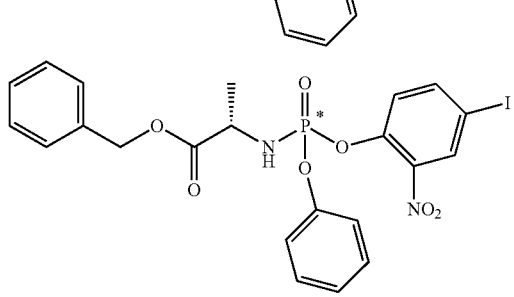

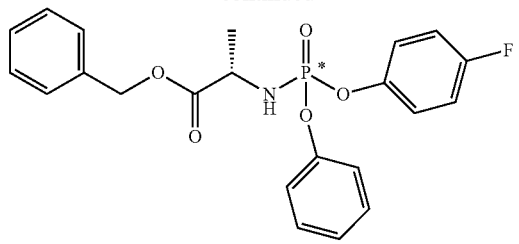
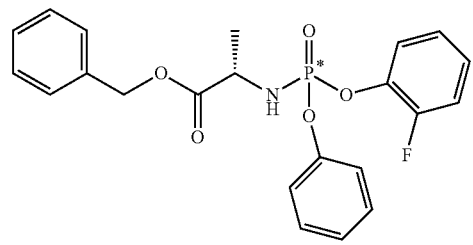
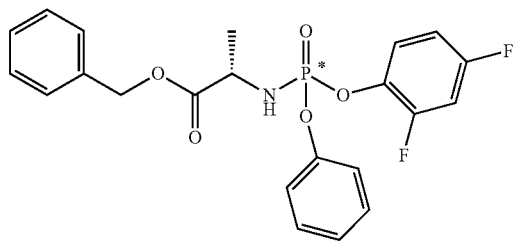
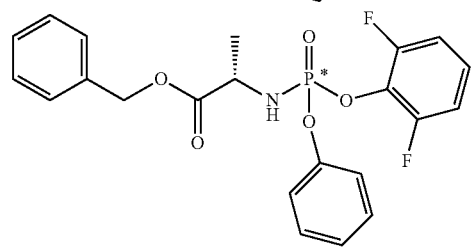
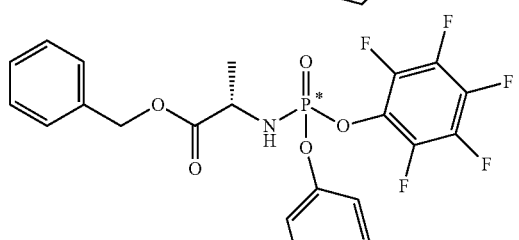
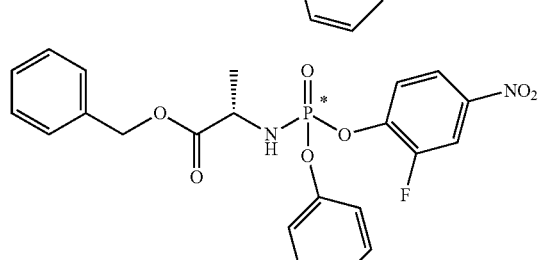
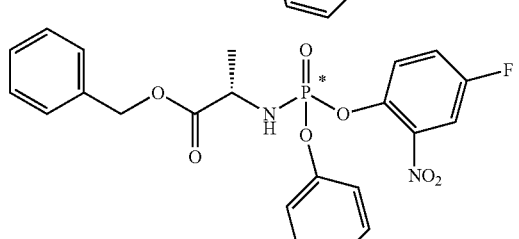
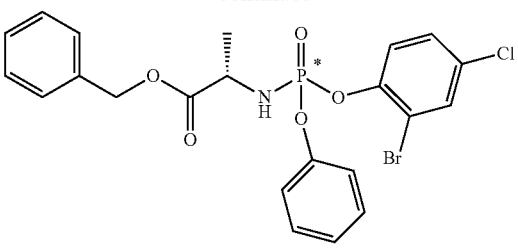
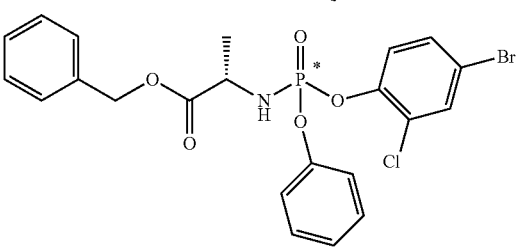
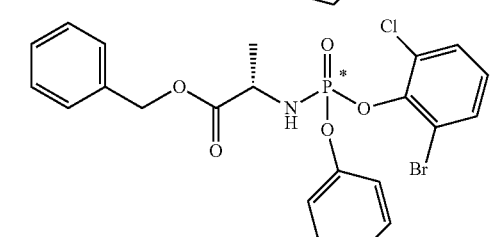
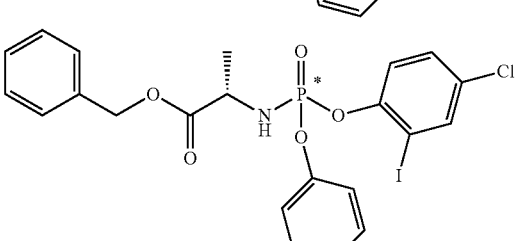
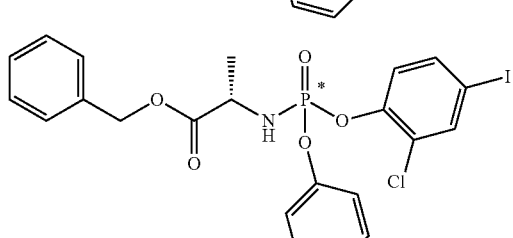
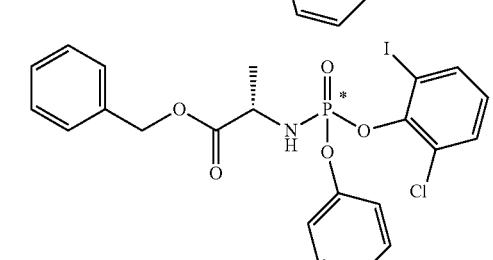
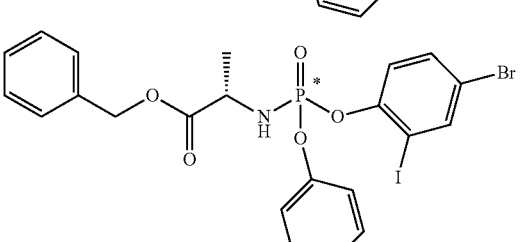

15
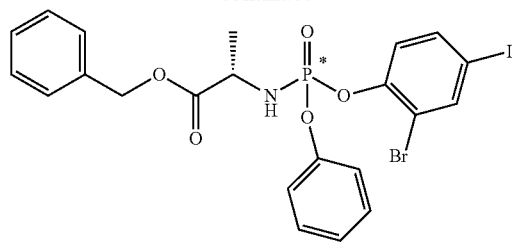
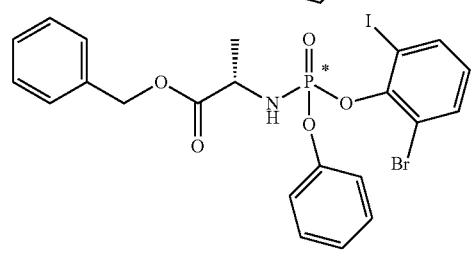
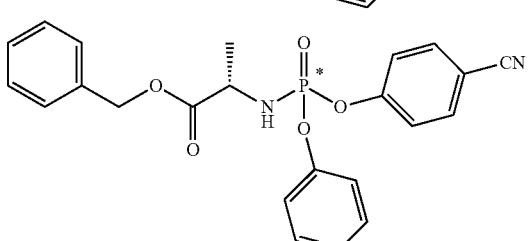
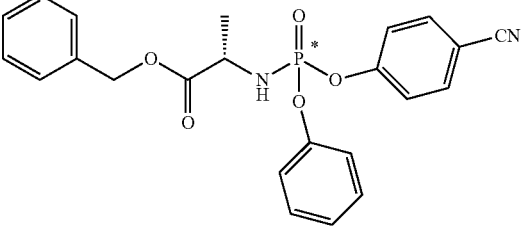
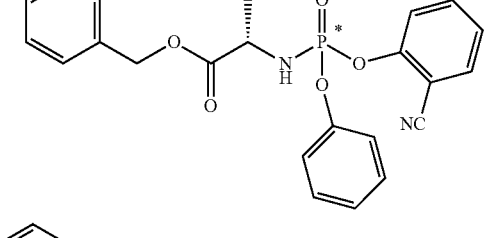
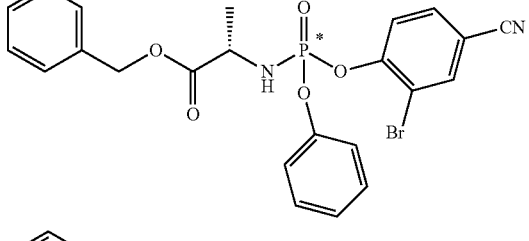
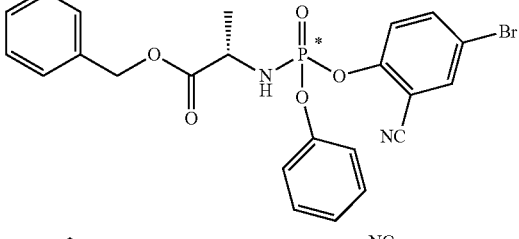
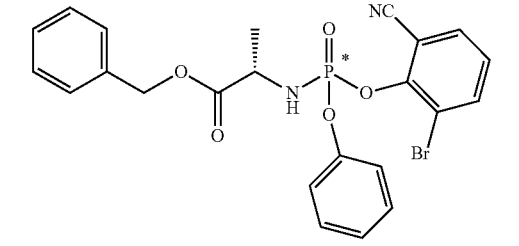
16
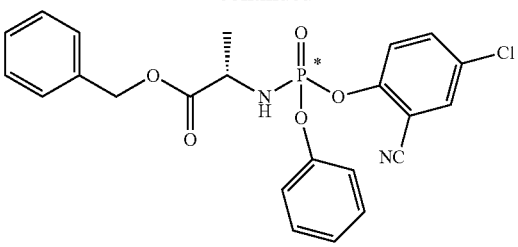
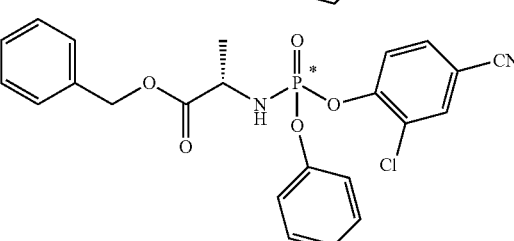
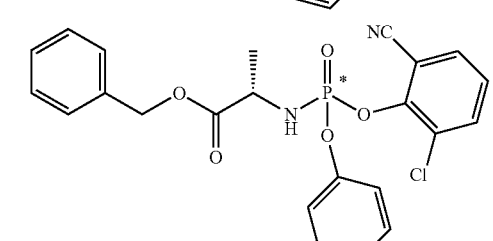
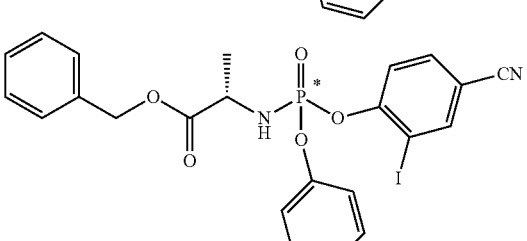
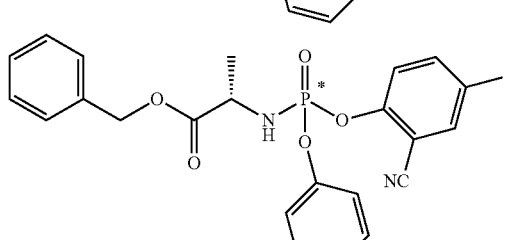
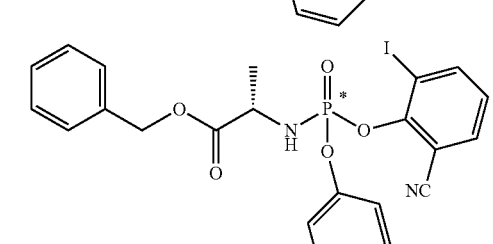
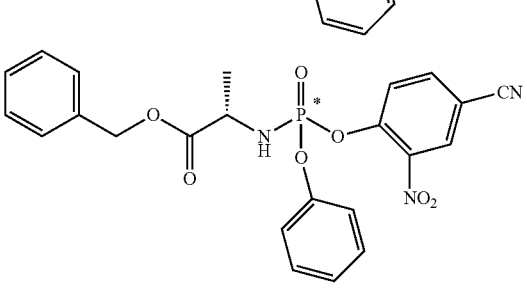

-continued
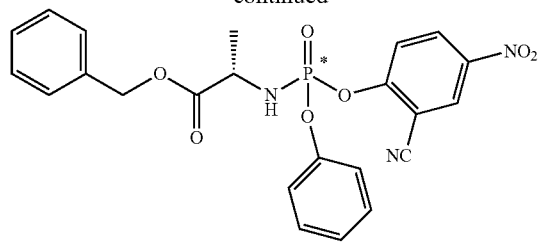
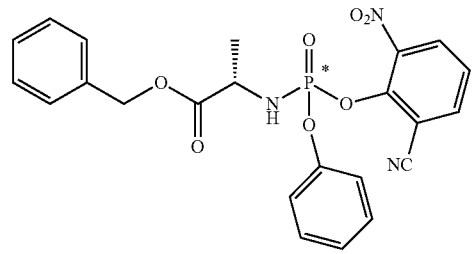
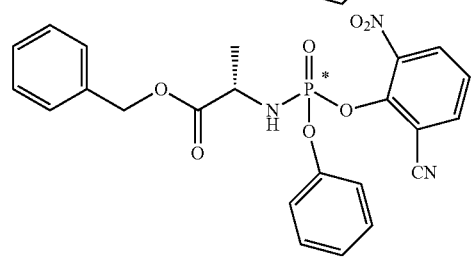
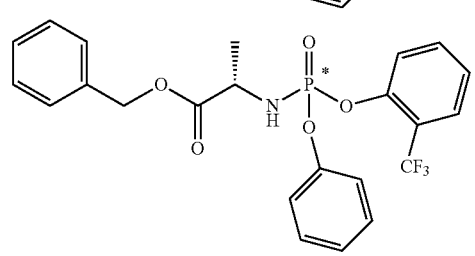
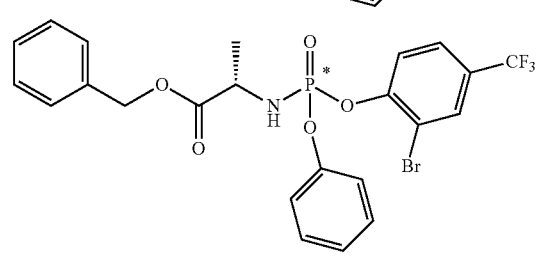
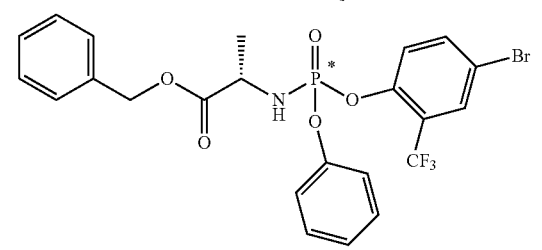
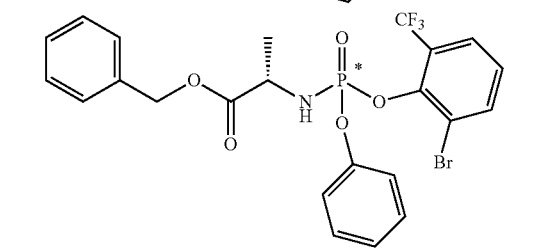
-continued
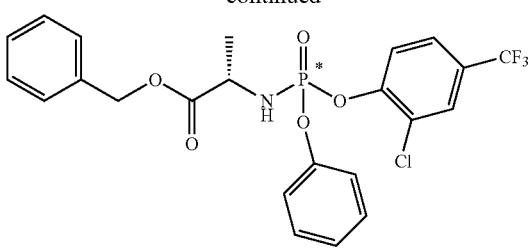
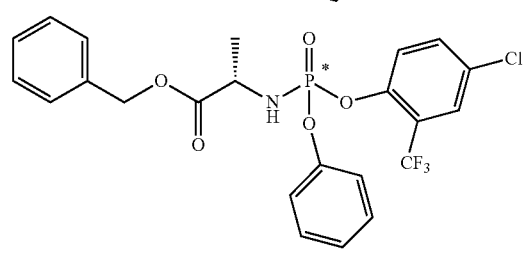
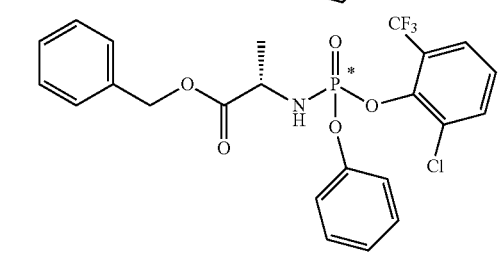
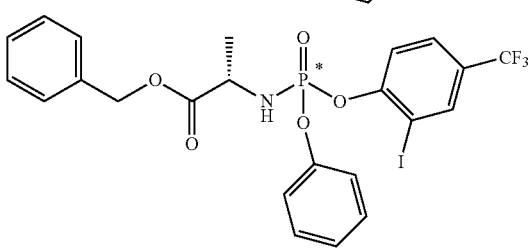
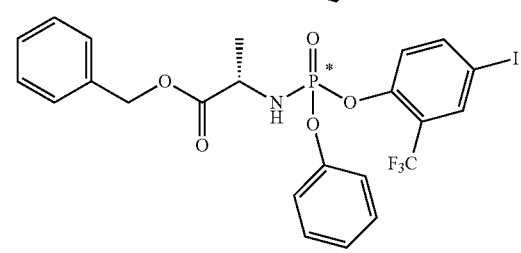
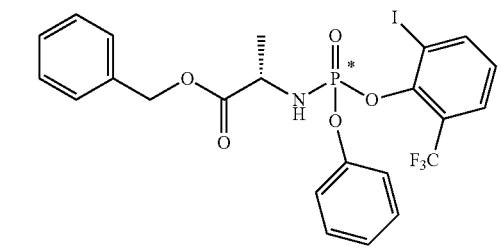
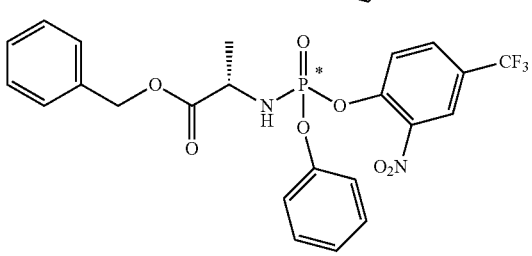

-continued

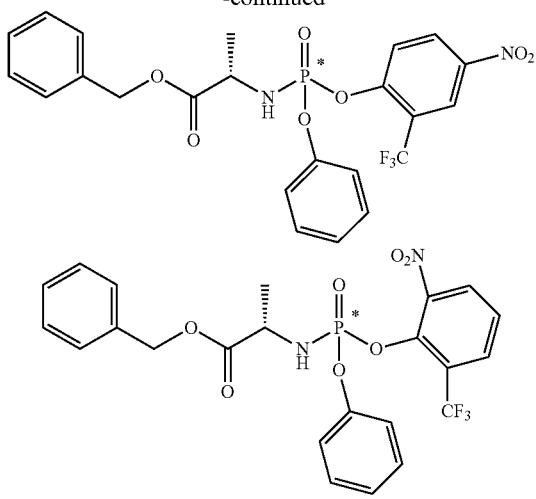

* represents chiral centre at the phosphorous

The compound of formula (VIII) may be:

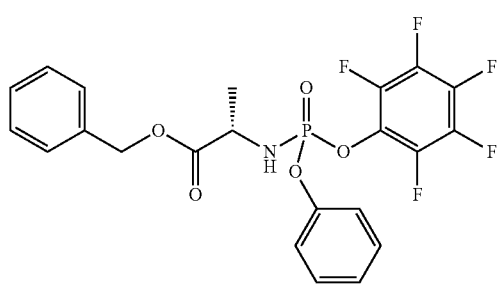 [SMILES: C[C@H](NP(=O)(Oc1ccccc1)Oc1c(F)c(F)c(F)c(F)c1F)C(=O)OCc1ccccc1]

The compound of formula (VIII) may be:

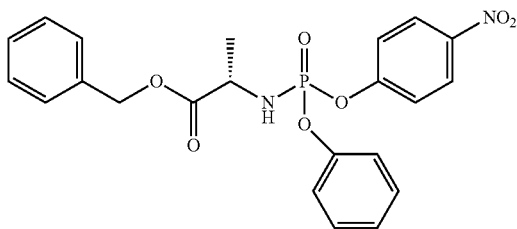 [SMILES: C[C@H](NP(=O)(Oc1ccccc1)Oc1ccc([N+](=O)[O-])cc1)C(=O)OCc1ccccc1]

Step e) may be conducted in an organic solvent (S1). Organic solvents include but are not limited to ethers (e.g. tetrahydrofuran, dioxane, diethyl ether, methyl-t-butylether); ketones (e.g. acetone and methyl isobutyl ketone); halogenated solvents (e.g. dichloromethane, chloroform and 1,2-dichloroethane); and amides (e.g. DMF, NMP); or mixtures thereof. Where step a) is conducted in the presence of a Grignard reagent, the organic solvent is preferably an ether. Most preferably, the solvent is tetrahydrofuran.

Where step e) of the first aspect is conducted in the present of a nitrogen base, the organic solvent is most preferably a halogenated solvent or an amide.

The reaction is typically conducted at a suitable temperature, e.g from about −5° C. to about 40° C. Preferably, the reaction temperature is about 25° C. to about 30° C. The reaction may be allowed to stir for a period of time from about 15 mins to about 16 h and preferably from about 30 mins to about 60 mins.

Step f)

Where two or more of $P^2$, $P^3$ and $P^4$ are protecting groups, the deprotection step f) may comprise two or three individual deprotection reactions. This is the case where two or three different protecting groups are used and where those two or three protecting groups cannot be removed under the same conditions.

It may be, however, that the deprotection step comprises a single deprotection reaction (step f) in which all protecting groups are removed. Thus, it may be that $P^2$, $P^3$ and $P^4$ are protecting groups which can be removed under the same conditions. It may be that $P^2$, $P^3$ and $P^4$ are the same.

Where a protecting group is acid sensitive (e.g. trityl, C(O)OtBu, MOM, MEM, 2,4-dimethoxybenzyl, 2,3-dimethoxybenzyl, —C(Me)$_2$—) the deprotection step can be conducted using a suitable acid. The acid may be a Bronsted acid (e.g. TFA, phosphoric acid, HCl, or formic acid) or a Lewis acid (e.g. $ZnBr_2$, $CeCl_3$). Lewis acids (e.g. $ZnBr_2$) are less preferred. HCl is likewise less preferred. Preferably, the acid is TFA.

Where a protecting group is base sensitive, e.g. acetyl, benzoyl, the deprotection step can be conducted using a suitable base, e.g. aqueous $NH_3$ or aqueous NaOH. Base sensitive groups may be less preferred.

Where a protecting group is a silyl group (e.g. triethylsilyl or t-butyldimethylsilyl, the deprotection step can be conducted using a suitable acid (e.g. TFA, PPTS, TsOH, acetic acid, citric acid) or using a suitable fluorine source (e.g. tetrabutylammonium fluoride, fluorosilicic acid, HF).

Where a protecting group is a benzyl group or a C(O)Obenzyl group, the deprotection step can be conducted using $H_2$ and a suitable catalyst (e.g. Pd/C). Such protecting groups may be less preferred.

Where a protecting group is a 4-methoxy-benzyl, 2,3-dimethoxybenzyl, 2,4-dimethoxybenzyl or C(O)O-(4-methoxybenzyl) the deprotection step can be performed using a suitable oxidizing agent (e.g. meta-chloroperbenzoic acid).

Where a protecting group is —C(O)—O-allyl, the deprotection step can be performed using $(PPh_3)_4Pd$.

Where a protecting group is —C(O)—O—$CH_2$-fluorenyl, the deprotection step can be performed using piperidine.

The deprotection step may be conducted in an organic solvent or a mixture thereof. Exemplary organic solvents include, but are not limited to halogenated solvents (e.g. dichloromethane, chloroform, dichloroethane); alcohols (e.g. methanol, ethanol, isopropanol) and ethers (e.g. tetrahydrofuran, diethyl ether).

Where the deprotection step is carried out in the presence of an acid (e.g. TFA), the organic solvent is preferably a halogenated solvent, e.g. dichloromethane.

The deprotection reaction may be carried out at a temperature in the range of, for example −10° C. to about 30° C., e.g. to about 10° C. A convenient temperature to carry out the reaction is −5° C. to 5° C. The reaction may be allowed to stir for a period of time from about 15 mins to about 16 hours and preferably from about 1 hour to about 4 hours, and more preferably from about 2 hours to about 3 hours.

Steps a) and c)

The introduction of protecting groups $P^1$ and $P^2$ can typically be added and removed using conventional protecting group methodology, for example, as described in "Protective Groups in Organic Chemistry," edited by J W F McOmie (1973); "Protective Groups in Organic Synthesis," 2nd edition, T W Greene (1991); and "Protecting Groups", 3rd addition P. J Koscienski (1995).

In particular, where $P^1$ and/or $P^2$ are silyl, they can be introduced using a silylating agent comprising the desired silyl group and a leaving group, such as a halide or a sulfonate, in the presence of a base (e.g. an amine base). The leaving group of the silylating agent may be a halide, e.g. chloride, or it may be triflate. The silylating agent may be TBDMSCl.

The base may be a trialkyl amine (e.g. TEA, DIPEA) or it may be a nitrogen heterocycle (e.g. imidazole or pyridine).

The solvent may be selected from DCM and DMF.

Step b)

The source of hydride will typically be a hydride reducing agent. Preferably, the source of hydride is LiEt$_3$BH.

If the 5'-hydroxy is not protected during the epoxide opening step, cordycepin is formed. Cordycepin is highly water soluble meaning that extraction from the reaction mixture could not be done without also recovering significant amounts of inorganic impurities. These could be separated from the cordycepin using well known techniques but this is resource intensive and can lead to yield loss. For this reason, the 5'-hydroxy group is most optimally protected before opening the epoxide. The ring opened product (5'protected cordycepin) can then be isolated from the reaction mixture using an organic solvent (e.g. EtOAc). With this change relative to prior art syntheses of NUC-7738, the yield for epoxide opening was increased to 90% from 65%.

In a second aspect of the invention is provided ($S_p$)-NC-7738:

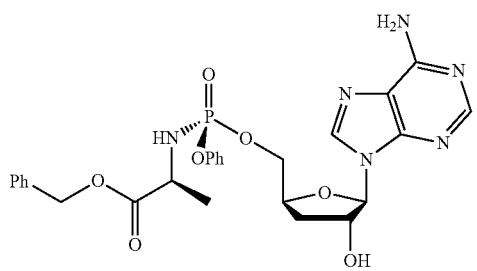 [SMILES: C[C@H](N[P@](=O)(OC[C@@H]1C[C@H](O)[C@H](n2cnc3c(N)ncnc32)O1)Oc1ccccc1)C(=O)OCc1ccccc1]

in substantially diastereoisomerically pure form. The preferential isomerization to form the (S)-diastereoisomer of the compound of formula (VIII), means that the $S_p$ isomer of NUC-7738 is easier to produce than the $R_p$ isomer.

In an third aspect of the invention is provided ($R_p$)-NUC-7738:

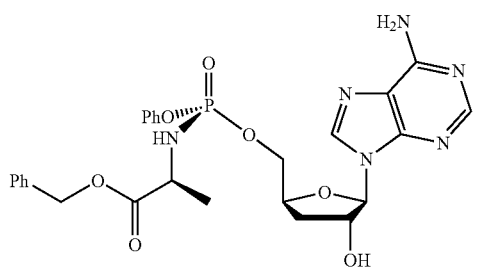 [SMILES: C[C@H](N[P@@](=O)(OC[C@@H]1C[C@H](O)[C@H](n2cnc3c(N)ncnc32)O1)Oc1ccccc1)C(=O)OCc1ccccc1]

in substantially diastereoisomerically pure form.

The invention may also provide a pharmaceutical composition comprising a compound of the second and third aspects of the invention and a pharmaceutically acceptable excipient.

The invention may also provide a method of treating cancer (e.g. a solid tumour or leukaemia), the method comprising administering to a subject in need thereof a therapeutically effective amount of a compound of the second and third aspects of the invention.

The compounds of the second and third aspects of the invention may be for medical use. The compounds of the second and third aspects of the invention may be for use in treating cancer (e.g. a solid tumour or leukaemia).

The products of the second and third aspects of the invention may be obtainable by (or obtained by) the first aspect of the invention.

DETAILED DESCRIPTION

The group optionally substituted —Si($C_1$-$C_6$-alkyl)$_3$ may be a —Si($C_1$-$C_4$-alkyl)$_3$ group. The group is (i.e. the alkyl groups are) preferably unsubstituted. Illustrative examples include triethylsilyl and t-butyl-dimethylsilyl.

The group optionally substituted —C(O)—$C_1$-$C_6$-alkyl may be a —C(O)—$C_1$-$C_4$-alkyl group. The group (i.e. the alkyl group) is preferably unsubstituted. Illustrative examples include acetyl and propionyl.

The group optionally substituted —C(O)-aryl may be a —C(O)-phenyl group. The group (i.e. the phenyl group) is preferably unsubstituted. Illustrative examples include benzoyl.

The group optionally substituted —C(O)—$C_1$-$C_6$-alkyl may be a —C(O)—O$C_1$-$C_4$-alkyl group. The group (i.e. the alkyl group) is preferably unsubstituted. Illustrative examples include —C(O)—O-methyl and —C(O)—O-ethyl. A particularly preferred example is C(O)OtBu.

The group optionally substituted —($C_1$-$C_3$-alkylene)-aryl is preferably an optionally substituted benzyl group. Illustrative examples include benzyl, phenethyl, 4-methoxy benzyl, 4-nitrobenzyl, 4-bromobenzyl, 2,3-dimethoxybenzyl and 2,4-dimethoxybenzyl.

The group optionally substituted —C(O)OCH$_2$-aryl is preferably an optionally substituted —C(O)Obenzyl group. Illustrative examples include —C(O)Obenzyl and —C(O)O-(4-methoxybenzyl).

The group optionally substituted —$C_1$-$C_4$-alkyl-O—$C_1$-$C_4$-alkyl may be a —$C_1$-$C_2$-alkyl-O—$C_1$-$C_2$-alkyl group. The group is (i.e. the alkyl groups are) preferably unsubstituted. Illustrative examples include methoxy-methyl (MOM) and 2-methoxy-ethoxy-methyl (MEM).

The group optionally substituted —S(O)$_2$—$C_1$-$C_6$-alkyl may be a —S(O)$_2$—$C_1$-$C_4$-alkyl group. The group (i.e. the alkyl group) is preferably unsubstituted. Illustrative examples include methanesulfonate.

The group optionally substituted —S(O)$_2$-aryl may be a —S(O)$_2$-phenyl group. Illustrative examples include phenylsulfonate, 4-methylphenylsulfonate and 4-nitro phenylsulfonate.

The group optionally substituted —C(aryl)$_3$ may be a —C(phenyl)$_3$ group. Illustrative examples include trityl.

Throughout this specification, 'diastereomerically enriched form' and 'substantially diastereomerically pure form' means a diastereoisomeric purity of greater than 95%. 'Diastereomerically enriched form' and 'substantially diastereomerically pure form' may mean a diastereoisomeric purity of greater than 98%, greater than 99% or greater than 99.5%.

Any of the aforementioned alkyl and aryl (e.g. phenyl, including the phenyl groups in benzyl groups) groups, are optionally substituted, where chemically possible, by 1 to 3 substituents which are each independently at each occurrence selected from the group consisting of: oxo, =NR$^a$, =NOR$^a$, halo, nitro, cyano, NR$^a$R$^a$, NR$^a$S(O)$_2$R$^a$, NR$^a$CONR$^a$R$^a$, NR$^a$CO$_2$R$^a$, OR$^a$; SR$^a$, SOR$^a$, SO$_3$R$^a$, SO$_2$R$^a$, SO$_2$NR$^a$R$^a$, CO$_2$R$^a$ C(O)R$^a$, CONR$^a$R$^a$, C$_1$-C$_4$-allkyl, C$_2$-C$_4$-alkenyl, C$_2$-C$_4$-alkenyl, and C$_1$-C$_4$ haloalkyl; wherein R$^4$ is independently at each occurrence selected from H, C$_1$-C$_4$ alkyl and C$_1$-C$_4$ haloalkyl.

It may be that any of the aforementioned alkyl groups is unsubstituted.

It may be that any of the aforementioned aryl groups (e.g. phenyl, including the phenyl groups in benzyl groups) are optionally substituted, where chemically possible, by 1 to 3 substituents which are each independently at each occurrence selected from the group consisting of: halo, nitro, cyano, NR$^a$R$^a$, NR$^a$S(O)$_2$R$^a$, NR$^a$CONR$^a$R$^a$, NR$^a$CO$_2$R$^a$, OR$^a$; SR$^a$, SOR$^a$, SO$_3$R$^a$, SO$_2$R$^a$, SO$_2$NR$^a$R$^a$, CO$_2$R$^a$ C(O)R$^a$, CONR$^a$R$^a$, C$_1$-C$_4$-alkyl, C$_2$-C$_4$-alkenyl, C$_2$-C$_4$-alkenyl, and C$_1$-C$_4$ haloalkyl; wherein R$^a$ is independently at each occurrence selected from H, C$_1$-C$_4$ alkyl and C$_1$-C$_4$ haloalkyl.

It may be that any of the aforementioned aryl (e.g. phenyl, including the phenyl groups in benzyl groups) groups are optionally substituted by 1 to 3 substituents which are each independently at each occurrence selected from the group consisting of: halo, nitro, OR$^a$; C$_1$-C$_4$-alkyl, C$_1$-C$_4$ haloalkyl; wherein R$^a$ is independently at each occurrence selected from H, C$_1$-C$_4$ alkyl and C$_1$-C$_4$ haloalkyl.

Aryl groups have from 6 to 20 carbon atoms as appropriate to satisfy valency requirements. Aryl groups are carbocyclic groups which satisfy the Huckel rule (i.e. they contain a carbocyclic ring system containing 2(2n+1)π electrons). Aryl groups may be optionally substituted phenyl groups, optionally substituted biphenyl groups, optionally substituted naphthalenyl groups or optionally substituted anthracenyl groups. Equally, aryl groups may include non-aromatic carbocyclic portions. Preferably an aryl group is an optionally substituted phenyl group.

Alkyl groups may be straight chain or branched. Thus, for example, a C$_4$ alkyl group could be n-butyl, i-butyl or t-butyl.

Where, a deprotection is performed in the presence of an acid (e.g. TFA), isolation of the product obtained after the deprotection is typically done by quenching the excess acid used in deprotection step and extracting the product with a water immiscible organic solvent and recovering the product by evaporation of the organic solvent.

Examples of water immiscible organic solvents useful in extraction include esters such as ethyl acetate, methyl acetate, isopropyl acetate and the like; chlorinated solvents such as dichloromethane, chloroform and the like; aromatic hydrocarbon solvents such as toluene, xylene and the like; preferably ethyl acetate.

In certain embodiments, it may be desirable to purify the ProTide obtained from the process of the first aspect of the invention. Methods of purification are well known to those skilled in the art and include chromatography (e.g. column chromatography), recrystallisation and distillation. In other embodiments, no purification is necessary.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

The following abbreviations are used throughout this specification:

| | |
|---|---|
| ACN - acetonitrile | AlBBr - acetoxy isobutyryl bromide |
| BOC - t-butylcarbonate | CAN - ceric ammonium nitrate |
| DCM - dichloromethane | |
| DIPEA - diisopropylethylamine | DMAP - N,N-dimethyl-4-aminopyridine |
| DMF - N,N-dimethylformamide | eq. - molar equivalents |
| FUDR - 5-fluoro-2'-deoxyuridine | IPA - isopropyl alcohol |
| MEM - 2-methoxyethoxymethyl | MOM - methoxymethyl |
| MTBE - methyl-t-butylether | NMP - N-methyl-2-pyrrolidone |
| Np - 1-naphthyl | PPTS - Pyridinium p-toluenesulfonate |
| PTSA - para-toluene sulfonic (tosic) acid | RT - room temperature |
| TBAF - tetrabutylammonium fluoride | TBDMS - tert-butyldimethylsilyl |
| TEA - triethylamine | Tf - trifluoromethylsulfonate (triflate) |
| TFA - trifluoroacetic acid | THF - tetrahydrofuran |
| TsOH - para-toluene sulfonic (tosic) acid | |

V is used to denote volume (in mL) per weight (in g) starting material. So if there was 1 g of starting material, 10 V would mean 10 mL of the indicated liquid.

EXAMPLES

The present invention is further illustrated by the following examples, which are provided by way of illustration only and should not be construed to limit the scope of the invention.

Example 1: Preparation of Diastereoisomeric Mixture of 2-[(2,3,4,5,6-pentafluorophenoxy)-phenoxy-phosphoryl amino] Propionic Acid Benzyl Ester 5 (An illustrative example of a compound of formula (VIII))

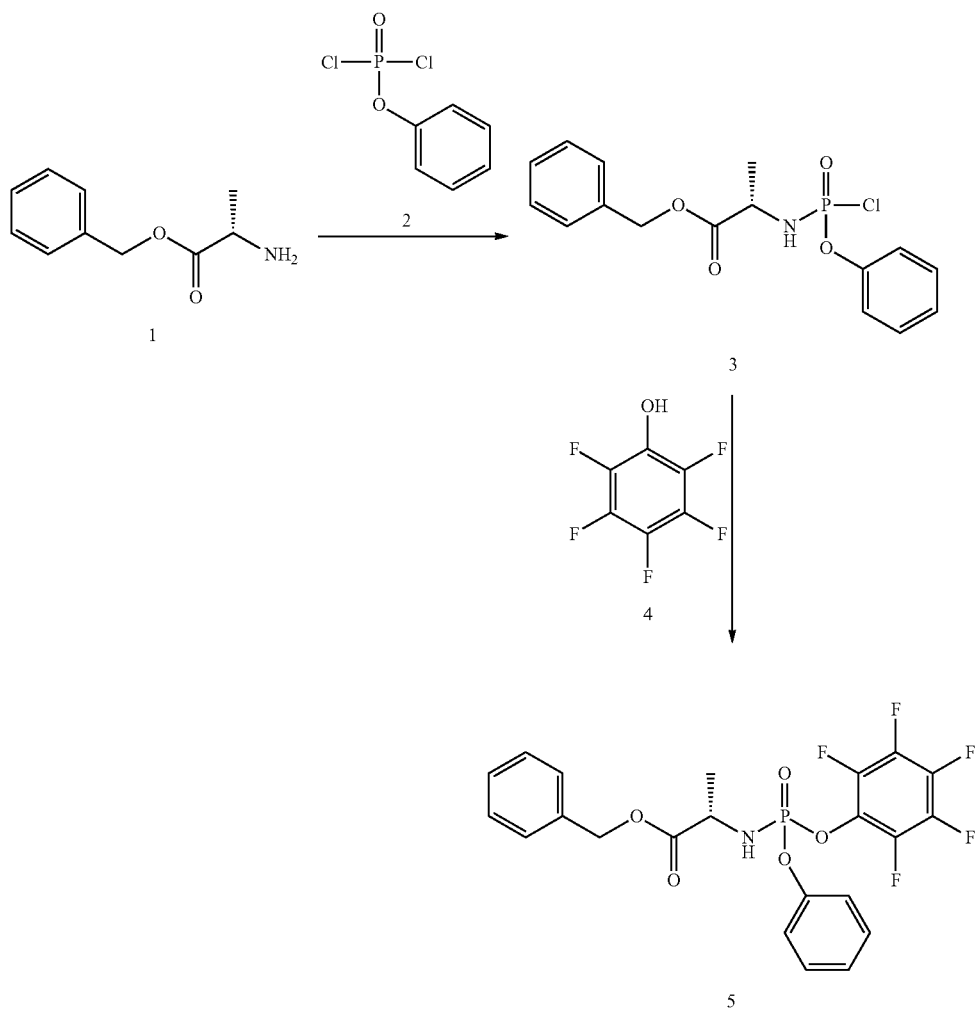

To a stirred mixture of L-alanine benzyl ester hydrochloride 1 (100 g) in methylene chloride (1 L) was added phenyl dichlorophosphate 2 (77 mL) at 25-35° C. and the resulting mixture was cooled to −70° C. to −78° C., triethylamine (130.5 mL) was added and the mixture was stirred for 1 hour at same temperature. Reaction mass temperature was raised to 25-35° C. and allowed to stir for 2 hours. After reaction completion, concentrated the reaction mass under vacuum at below 35° C. to obtain residue. To the obtained residue was added diisopropyl ether (2 L) at 25-35° C. and stirred for 30 min at same temperature. Filtered the reaction mass and washed with diisopropyl ether (500 mL) followed by concentrating the filtrate under vacuum at below 35° C. to obtain phenyl-(benzoxy-L-alaninyl)-phosphorochloridate 3. The obtained compound was dissolved in methylene chloride (1 L) at 25-35° C. and cooled to −5° C. to −10° C. To the reaction mass pentafluorophenol 4 (85.5 g), triethylamine (65.2 mL) were added at same temperature and stirred for 2 hrs. After reaction completion, concentrated the reaction mass under vacuum at below 35° C. and charged ethyl acetate (1 L) at 25-35° C. and stirred for 30 min at same temperature. Filtered the solids and washed with ethyl acetate (1 L). To the filtrate was given water (1 L), 10% sodium carbonate (2×1 L), brine (1 L) washings and dried the organic layer with anhydrous sodium sulphate, concentrated under vacuum at 35-45° C. to obtain diastereoisomeric mixture of title compound 5 as a white colored semi solid.

Yield: 210 g

Chiral Purity by HPLC (% area): 33.74:66.26% ($R_p$:$S_p$)

Example 2: Separation of $S_p$-Diastereoisomer of 2-[(2,3,4,5,6-pentafluorophenoxy)-phenoxy-phosphoryl amino] Propionic Acid Benzyl Ester 5 (An illustrative example of a compound of Formula (VIII))

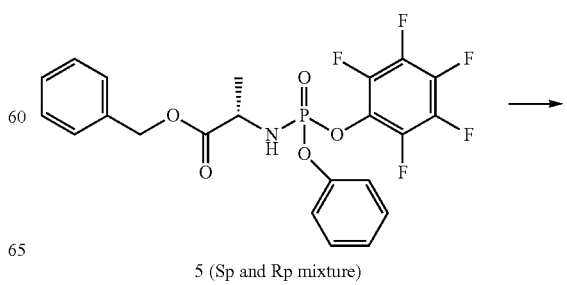

5 (Sp and Rp mixture)

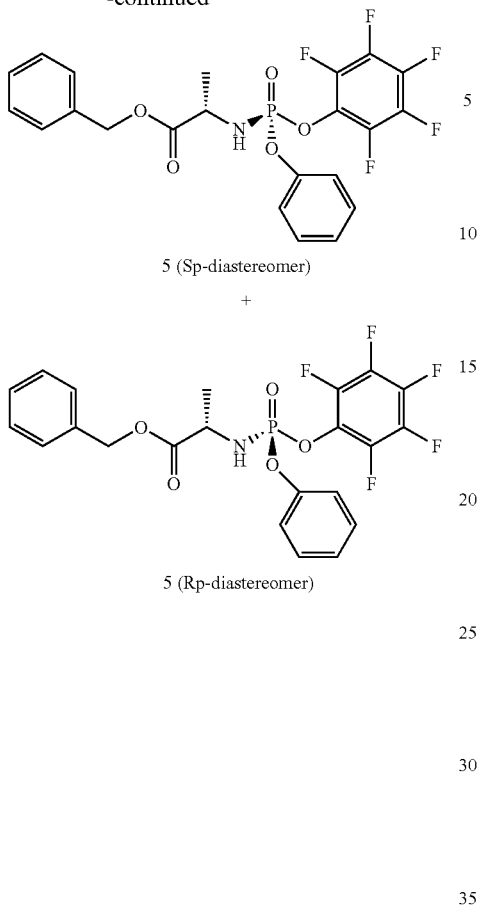

5 (Sp-diastereomer)

+

5 (Rp-diastereomer)

To a diastereoisomeric mixture of compound 5 (210 g; $R_p:S_p$—33.74:66.26%) was charged 20% ethyl acetate in hexane (1.2 L) at 25-35° C. and stirred for 1 hrs. Filtered the solids and washed with 20% ethyl acetate in hexane (300 mL) to obtain a mixture of diastereoisomeric mixture of compound 5.

Yield: 112 g

Chiral Purity by HPLC (% area): 22.13:77.87% ($R_p:S_p$)

Filtrate was concentrated under vacuum to obtain a diastereoisomeric mixture of compound of 5 (75 g; $R_p:S_p$—65.43:34.57%).

To a diastereoisomeric mixture of the compound of formula IIb (112 g; $R_p:S_p$—22.13:77.87%) was charged 20% ethyl acetate in hexane (1.2 lit) at 25-35° C. and stirred for 1 hrs. Filtered the solids and washed with 20% ethyl acetate in hexane (300 ml) to obtain substantially pure $S_p$-diastereoisomer of compound 5.

Yield: 80 g

Chiral Purity by HPLC (% area): 0.20:99.80% ($R_p:S_p$)

$^1$H NMR (300 MHz, DMSO-$d_6$): 7.18-7.41(m, 10H), 6.91-6.99(d, 1H), 5.10(s, 2H), 4.01-4.11(m, 1H), 1.30-1.32 (d, 3H)

ESI-MS (m/z): 524 (M+1)

Filtrate was concentrated under vacuum to obtain a diastereoisomeric mixture of compound 5 (28 g; $R_p:S_p$—80.77:19.23%).

Example 3: Enrichment of 2-[(2,3,4,5,6-pentafluorophenoxy)-phenoxy-phosphoryl amino] Propionic Acid Benzyl Ester 5 S-Isomer (An illustrative example of a compound of formula (VIII))

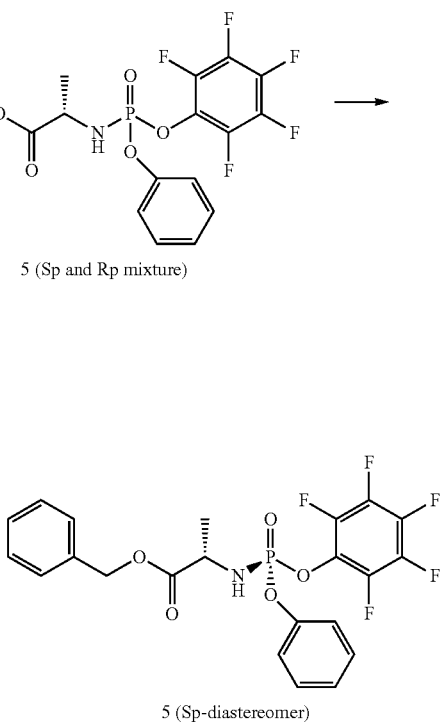

5 (Sp and Rp mixture)

→

5 (Sp-diastereomer)

To a stirred solution of 2-[(2,3,4,5,6-pentafluorophenoxy)-phenoxy-phosphoryl amino] propionic acid benzyl ester 5 (75 g; $R_p:S_p$—65.43:34.57%) in 20% ethyl acetate in hexane (1.1 L), triethyl amine (7.5 mL) was added at 25-35° C. and stirred for 6 hrs at same temperature. After reaction completion, reaction mass was quenched in to a water (750 mL) and extracted with ethyl acetate (750 mL). Organic layer was dried with anhydrous sodium sulphate and concentrated under vacuum to afford title compound as a solid.

Yield: 45 g

Chiral Purity by HPLC (% area): 91.29:8.71% ($S_p:R_p$)

To the above obtained $R_p$ and $S_p$-diastereoisomeric mixture of 2-[(2,3,4,5,6-pentafluorophenoxy)-phenoxy-phosphoryl amino] propionic acid benzyl ester 5 (45 g; $R_p:S_p$—8.71:91.29%) was slurred in 20% ethyl acetate in hexane (1.1 L) at 25-30° C. and stirred for 1 hr at same temperature. Filtered the solid and washed with 20% ethyl acetate in hexane (225 ml) to obtain $S_p$-diastereoisomer of the title compound as a solid.

Yield: 19 g

Chiral Purity by HPLC (% area): 99.92:0.08% ($S_p:R_p$)

Example 4: Preparation of Diastereoisomeric Mixture of 2-[(4-nitrophenoxy)-phenoxy-phosphorylamino] Propionic Acid Benzyl Ester 7 (an illustrative example of a compound of Formula (VIII)

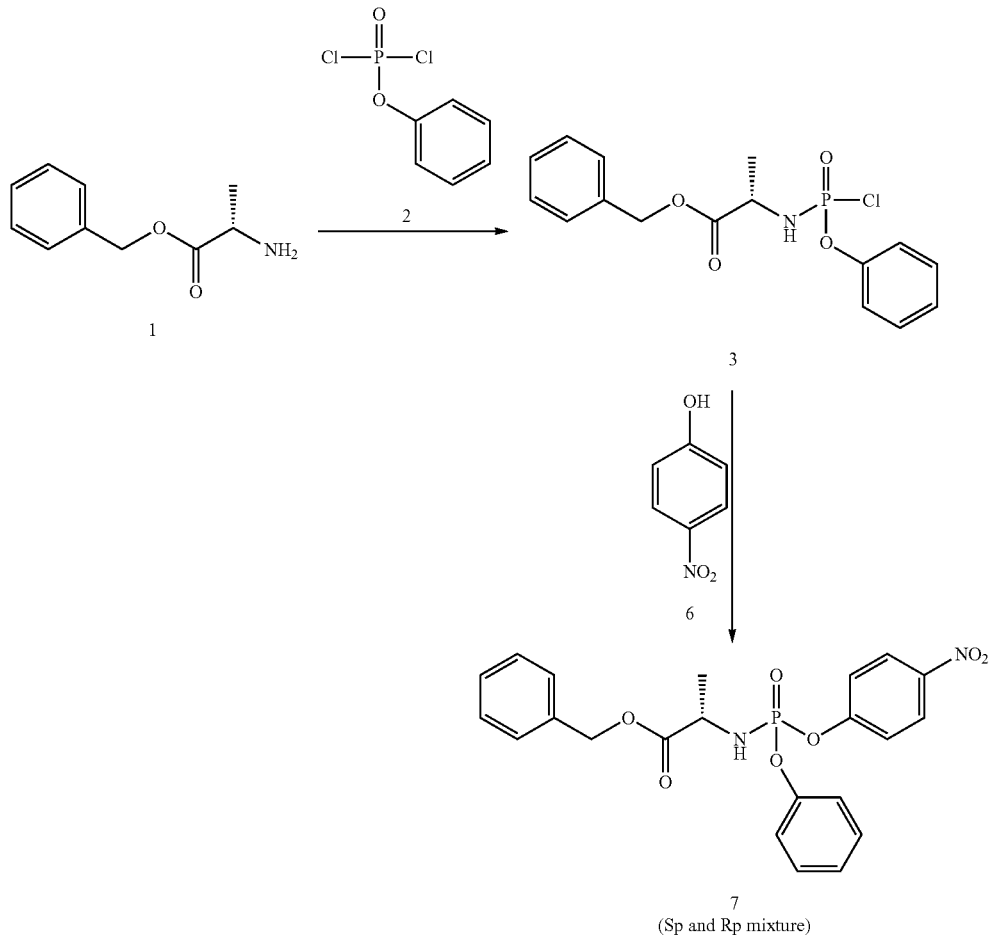

To a stirred mixture of L-alanine benzyl ester hydrochloride 1 (50 g) in methylene chloride (500 mL) was added phenyl dichlorophosphate 2 (54 g) at 25-35° C. and the resulting mixture was cooled to −70° C. to −78° C., added triethyl amine (65.2 mL) and stirred for 1 hour at same temperature. Reaction mass temperature was raised to 25-35° C. and allowed to stir for 2 hrs. After reaction completion, concentrated the reaction mass under vacuum at below 35° C. to obtain residue. To the obtained residue was added diisopropyl ether (1 L) at 25-35° C. and stirred for 30 min at same temperature. Filtered the reaction mass and washed with diisopropyl ether (250 mL) followed by concentrating the filtrate under vacuum at below 35° C. to obtain phenyl-(benzoxy-L-alaninyl)-phosphorochloridate 3. The obtained compound was dissolved in methylene chloride (500 mL) at 25-35° C. and cooled to −5° C. to −10° C. To the reaction mass 4-nitrophenol 6 (27.5 g), triethyl amine (65.2 mL) was added at same temperature and stirred for 2 hrs. After reaction completion, concentrated the reaction mass under vacuum at below 35° C. and charged ethyl acetate (500 mL) at 25-35° C. and stirred for 30 min at same temperature. Filtered the solids and washed with ethyl acetate (500 mL). To the filtrate was given water (500 mL), 10% sodium carbonate (2×500 mL), brine (500 mL) washings and dried the organic layer with anhydrous sodium sulphate, concentrated under vacuum at 35-40° C. to obtain diastereoisomeric mixture of title compound 7 as a thick oily liquid.

Yield: 90 g

Chiral Purity by HPLC (% area): 45.6:54.94% ($R_p$:$S_p$)

The above obtained diastereoisomeric mixture of 2-[(4-nitrophenoxy)-phenoxy-phosphorylamino] propionic acid benzyl ester 7 (40 g; $R_p$:$S_p$—45.6:54.94%) was separated in to pure $S_p$ and $R_p$ diastereoisomers by preparative HPLC and concentrated the pure fractions under vacuum to obtain $S_p$ and $R_p$ diastereoisomers separately.

Yield: $S_p$-diastereoisomer: 8 g,
$^1$H NMR (300 MHz, CDCl$_3$): 8.15-8.19 (d, 2H), 7.15-7.37 (m, 12H), 5.12 (s, 2H), 4.02-4.24 (m, 2H), 1.39-1.42 (d, 3H)

ESI-MS (m/z): 479 (M+Na)

$R_p$-diastereoisomer: 6 g,
$^1$H NMR (300 MHz, CDCl$_3$): 8.08-8.13 (d, 2H), 7.15-7.34 (m, 12H), 5.10 (s, 2H), 4.48-4.56 (m, 1H), 4.11-4.20 (m, 1H), 1.39-1.41 (d, 3H)

ESI-MS (m/z): 457 (M+1)$^+$ $S_p$ and $R_p$-diastereoisomers mixture: 20 g

Example 5—Preparation of (Sp)-2-[(2,3,4,5,6pentafluorophenoxy)-phenoxy-phosphoryl amino] Propionic Acid Benzyl Ester 5 (an illustrative example of a compound of formula (VIII))

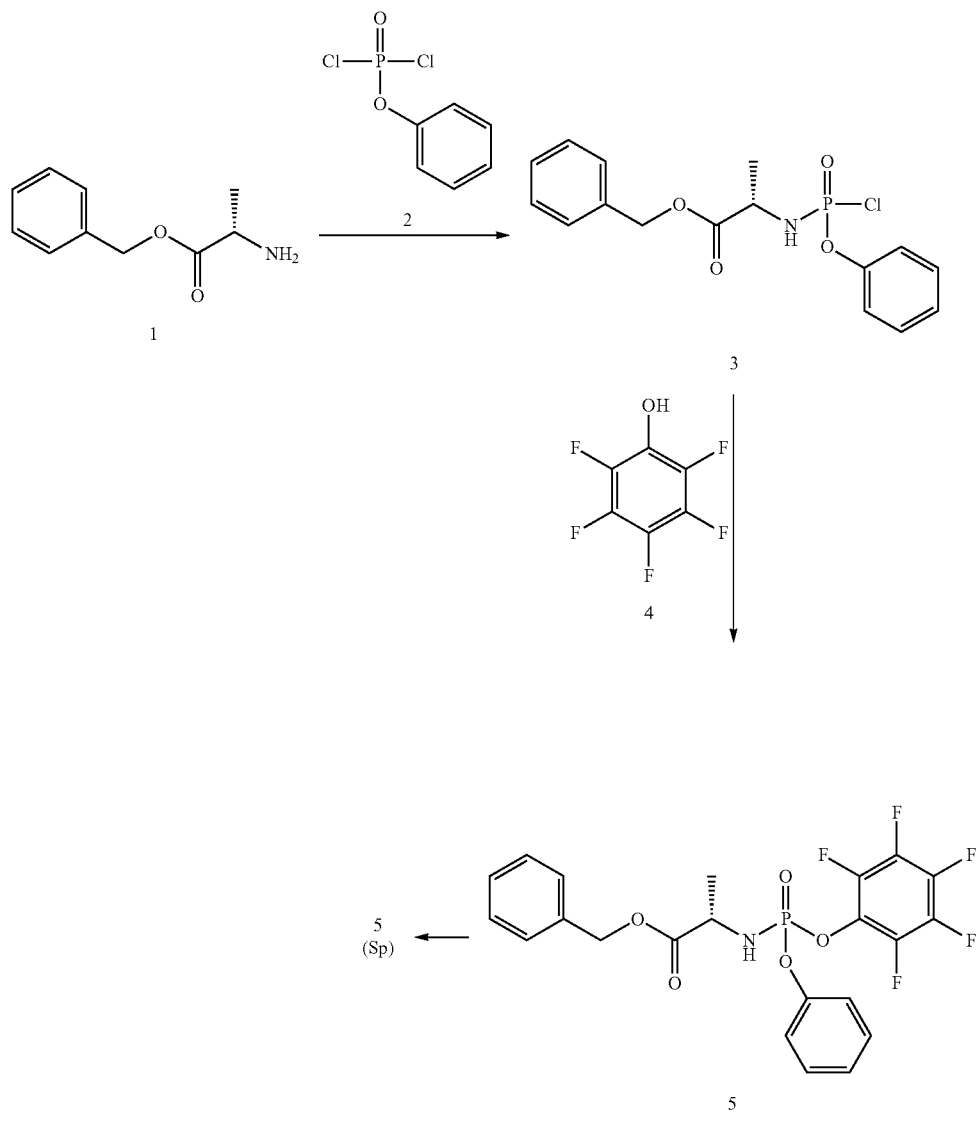

To a stirred mixture of L-Alanine Benzyl ester. HCl 1 (100 g) in 1000 mL of methylene dichloride was added phenyl dichlorophosphate 2 (97.8 g) into reaction mass at 30° C. The mixture was cooled to −20° C. and triethylamine (93.8 g) was added slowly, maintaining the temperature at −20° C. The reaction was stirred for 1 h at −20° C., then warmed to 10° C. (10±5) and stirred for a further 1.5 h.

A solution of pentafluorophenol 4 (85.3 g) in 100 mL of methylene dichloride was slowly added at 10° C. followed by trimethylamine (46.8 g) which is added slowly, maintaining the temperature at 10° C. Slowly add 46.9 g of triethylamine into reaction mass at 10° C. (10±5) under nitrogen atmosphere. The mixture was stirred for 2 h at 10° C. before being quenched by slow addition of 0.5 N HCl solution, maintaining the temperature at 10° C. After warming to room temperature the mixture was separated and the organics was washed with a saturated bicarbonate solution, distilled water and brine before being concentrated in vacuo.

The crude mixture was suspended in 1500 mL of 20% ethyl acetate in n-heptane at 25° C. Triethylamine (12.2 g) was added and the mixture was stirred at 25° C. The mixture was filtered and the solid dissolved in 2500 mL ethyl acetate which was washed with water and brine and concentrated in vacuo. The solid was suspended in 1200 mL of 20% ethyl acetate in n-heptane, stirred for 45-60 min and filtered. The material was dried under vacuum to provide the desired product 5-($S_p$). Yields are in the range 40 to 80% and the diastereoisomeric purity is over 99%.

Example 6—Formation of 2'-Protected Deoxyadenosine

2'-TBDMS protected 3'-deoxyadenosine 11 can be made according to the following scheme.

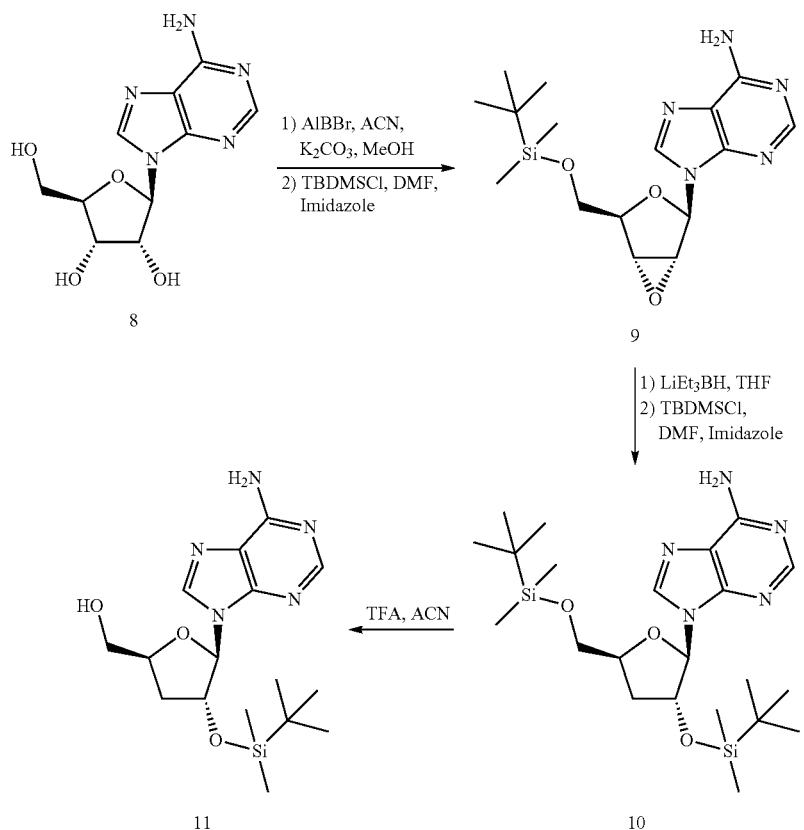

Adenosine (8) to Epoxide 9

One equivalent adenosine (8) was dissolved in 10 V acetonitrile and the mixture was cooled to 15° C. 3.0 molar equivalents acetoxy isobutyryl bromide was added slowly at 15° C. The mixture was warmed to room temperature and stirred for 8 hours. The reaction was quenched with sodium bicarbonate solution and extracted with ethyl acetate. The combined organic layers were washed with 5% sodium chloride solution and the organic layers were concentrated in vacuo.

The product was dissolved in 15 V methanol and 1 weight equivalent of potassium carbonate was added before stirring for 2 hours. The mixture was concentrated in vacuo and the product was washed with water before drying the product under vacuum at 60° C. to provide 2',3'-anhydro adenosine in a yield of 70-85%.

One equivalent of 2',3'-anhydro adenosine and 1.6 equivalents imidazole were dissolved in 5V DMF. The mixture was cooled to 15° C. and 0.8 equivalents TBDMSCl was added. The mixture was stirred for 1 to 2 hours at 30° C. before a further 0.4 equivalents imidazole and 0.4 equivalents TBDMSCl were added. The mixture was stirred for a further 1 to 2 hours at 30° C. before water was added (5V). The mixture was extracted with ethyl acetate. The combined organic layers were sequentially washed with 7% sodium bicarbonate solution, water and 5% sodium chloride solution before being concentrated in vacuo. The product was washed with heptane before being dried under vacuum at 50° C. to obtain epoxide 9 in 75-90% yield.

Epoxide 9 to 5'-Silyl Cordycepin 11

One equivalent of epoxide 9 was dissolved in a mixture of DMSO (5V) and THF (5V). The mixture was cooled to 0° C. and the mixture was purged with nitrogen gas. 1M Lithium triethylborohydride (1 eq) in THF was added at 0(±5)° C. over a period of 1-2 hours. The mixture was stirred at 0° C. for 30 minutes, warmed to 30° C. and stirred for 2 hours before methanol (10 V) was slowly added at 5° C. 10V 10% sodium hydroxide and then 10V 10% hydrogen peroxide solution were added drop wise at 5° C. The mixture was extracted with ethyl acetate and the combined organic layers were washed sequentially with 10% sodium metabisulfite solution, water in to reactor, 7% sodium bicarbonate solution and 10% sodium chloride solution before being concentrated in vacuo. The product was washed with heptane before being dried under vacuum at 50° C. to obtain 2'-silyl cordycepin in 70-100% yield.

The 2'-silyl cordycepin, 2.5 equivalents imidazole and 0.15 equivalents DMAP were dissolved in 5V DMF. The mixture was cooled to 15° C. before 2.5 equivalents TBDMSCl were added portionwise. The reaction was stirred for 4 hours at 30° C. before being cooled to 15° C. 10V water was added and the mixture was extracted with ethyl acetate. The organic layers were washed with 7% sodium bicarbonate solution, water and 5% sodium chloride before being concentrated in vacuo.

The mixture was dissolved in 8V acetonitrile and 2V water was added before the mixture was cooled to 0° C. 2.5 Eq. trifluoroacetic acid was added to the reaction mixture at 0° C. over a period of 30-60 min. The mixture was warmed to 10° C. and stirred for 4 to 6 hours at 10° C. Water was added and the mixture was extracted with ethyl acetate. The combined organic layers were washed with 7% sodium bicarbonate solution, water (twice) and 5% sodium chloride solution before being concentrated in vacuo. The product was washed with heptane and dried under vacuum to provide 5'-silyl cordycepin 11 in 40-70% yield.

Example 7—Formation of $S_p$ and $R_p$ Isomers of NUC-7738
Compound 11 can then be coupled with a compound of formula VIII
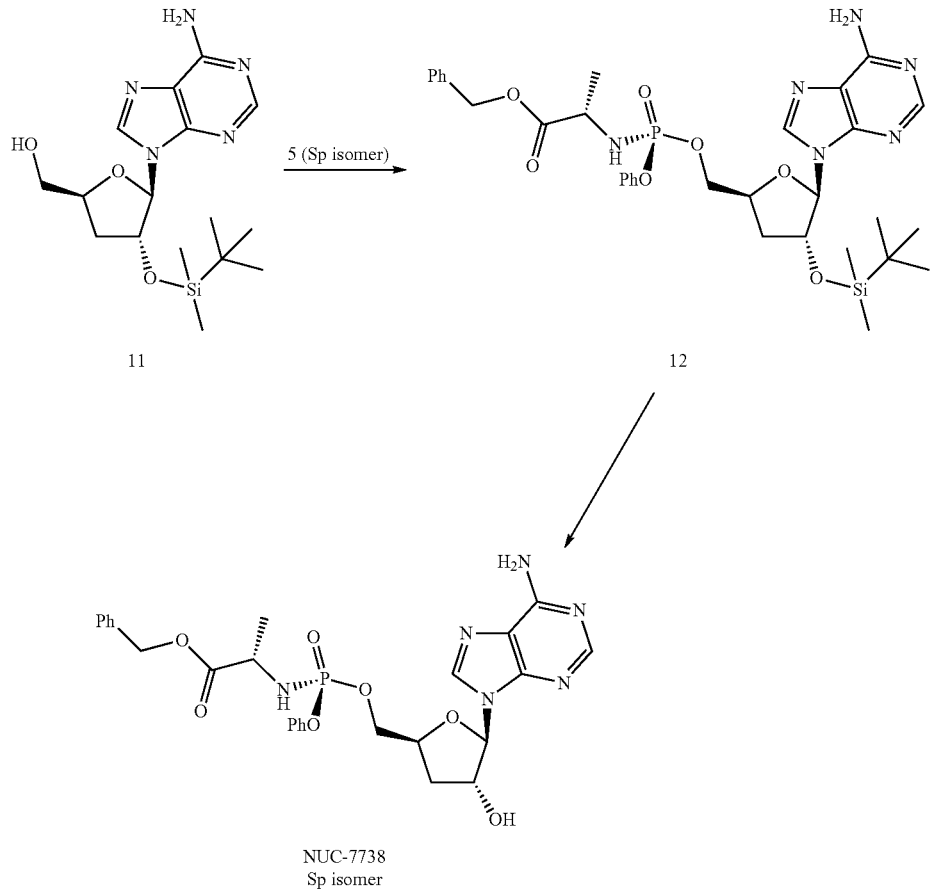
To form NUC-7738, the TBDMS group can be removed using TFA in THF.
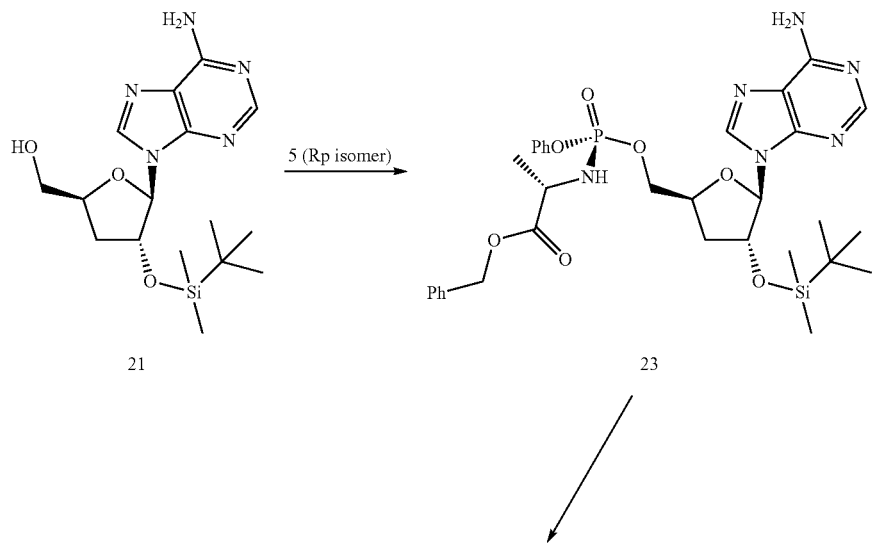

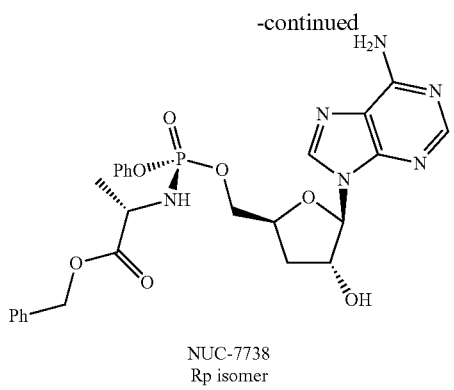

NUC-7738
Rp isomer

5'-Silyl Cordycepin 11 to $S_p$-NUC-7738

5'-silyl cordycepin 11 was dissolved in 10 V THF and cooled to 0° C. 2.0M t-BuMgCl (2.5 equivalents) was added and the mixture was stirred for 15 min. The $S_p$ isomer of compound 5 (2.5 eq) was dissolved in 5 V THF and was added to the reaction at 0° C. The mixture was stirred at 0° C. for 15 min before being warmed to 25° C. and stirred for a further 2 hours. The reaction was quenched into 10% ammonium chloride solution (10 vol) and extracted with ethyl acetate. The combined organic layers were washed with water and 10% brine solution before being concentrated in vacuo.

The product was dissolved in THF (10V) before being cooled to 0° C. A 10 V TFA and water (1:1) mixture was added to the reaction over a period of 30 min before the mixture was stirred for 45 min, warmed to 30° C. and stirred for a further 16 h. The reaction was quenched into 7% NaHCO$_3$ solution (90 V) at 0° C. before being extracted with ethyl acetate. The combined organic layers were washed with water, 7% sodium bicarbonate solution and 10% brine solution before being concentrated in vacuo.

The product was purified by column chromatography by using silica gel (100-200 mesh), the column was eluted by 2 to 10% MeOH in DCM to provide $S_p$-NUC-7738 in 40% yield. The HPLC purity of the product was 99.50% and Chiral HPLC showed the $S_p$ isomer to be present in 99.90% and the $R_p$ isomer to be present in 0.10%.

The same procedure can be carried out to provide $R_p$-NUC-7738.

Rp-NUC-7738:

$^1$H NMR (500 MHz, CDCl$_3$) $\delta_H$ 8.26 (s, 1H, H8), 8.22 (s, 1H, H2), 7.37-7.25 (m, 7H, Ar), 7.22-7.12 (m, 3H, Ar), 6.01 (d, J=1.5 Hz, 1H, H1'), 5.12 (AB q, $J_{AB}$=12.0 Hz, $\Delta\delta_{AB}$=0.04, 2H, CH$_2$Ph), 4.74-4.70 (m, 1H, H2'), 4.69-4.62 (m, 1H, H4'), 4.44-4.38 (m, 1H, H5'), 4.28-4.21 (m, 1H, H5'), 3.99-3.90 (m, 1H, CHCH$_3$ L-Ala), 2.35-2.27 (m, 1H, H3'), 2.09-2.02 (m, 1H, H3'), 1.29 (d, J=7.0 Hz, 3H, CHCH$_3$ L-Ala).

$^{31}$P NMR (202 MHz, CD$_3$OD) $\delta_p$ 3.91.

MS (ES$^+$) m/z found 569.2 [M+H$^{30}$], 591.2 [M+Na$^+$], 1159.4 [2M+Na$^+$] C$_{26}$H$_{29}$N$_6$O$_7$P required m/z 568.2 [M].

HPLC Reverse-phase HPLC (Varian Pursuit XRs 5 C18, 150×4.6 mm) eluting with H$_2$O/CH$_3$CN from 90/10 to 0/100 in 30 minutes, F: 1 mL/min, λ=200 nm, shows one peak with $t_R$ 14.02 min.

Sp-NUC-7738:

$^1$H NMR (500 MHz, CDCl$_3$) $\delta_H$ 8.24 (s, 1H, H8), 8.22 (s, 1H, H2), 7.36-7.26 (m, 7H, Ar), 7.22-7.13 (m, 3H, Ar), 6.01 (d, J=1.5 Hz, 1H, H1'), 5.08 (AB q, $J_{AB}$=12.0 Hz, $\Delta\delta_{AB}$=0.01, 2H, CH$_2$Ph), 4.70-4.67 (m, 1H, H2'), 4.66-4.60 (m, 1H, H4'), 4.41-4.35 (m, 1H, H5'), 4.26-4.19 (m, 1H, H5'), 4.02-3.94 (m, 1H, CHCH$_3$ L-Ala), 2.36-2.27 (m, 1H, H3'), 2.08-2.01 (m, 1H, H3'), 1.34-1.30 (m, 3H, CHCH$_3$ L-Ala).

$^{31}$P NMR (202 MHz, CD$_3$OD) $\delta_p$ 3.73. MS (ES$^+$) m/z found 569.2 [M+H$^+$], 591.2 [M+Na$^+$], 1159.4 [2M+Na$^+$] C$_{26}$H$_{29}$N$_6$O$_7$P required m/z 568.2 [M].

HPLC Reverse-phase HPLC (Varian Pursuit XRs 5 C18, 150×4.6 mm) eluting with H$_2$O/CH$_3$CN from 90/10 to 0/100 in 30 minutes, F: 1 mL/min, λ=200 nm, shows one peak with $t_R$ 14.26 min.

The stereochemistry ($R_p$ vs $S_p$) of the two NUC-7738 isomers described above has been confirmed by conventional X-ray crystallographic analysis.

Example 8

Four equivalents of L-alanine benzyl ester HCl salt were dissolved in DCM (30V) and 4.40 Eq. dichloride XX was added. The reaction was cooled to −20° C. and 8.0 Eq. TEA was added over a period of 60-120 min before the reaction was stirred for 1 hour at −20(±5)° C. The mixture was warmed to 30° C. and stirred for a further 1 to 2 before being concentrated in vacuo. The product was dissolved in MTBE, filtered and concentrated in vacuo before being cooled to 0° C. and dissolved in THF (5V). In a second vessel, compound 11 (1 equivalent) was dissolved in THF, the solution was cooled to 0° C. before 4.0 Eq tertiary butyl magnesium chloride (2M in THF) was added over a period of 60-120 min at 0 C. The solution obtained in the previous paragraph was dissolved added at 0° C. over a period of 30-60 min and the mixture was stirred at 5° C. for 1 to 2 hours.

10% ammonium chloride solution was added at 5° C. over a period of 60-120 min, the mixture was then warmed and extracted with ethyl acetate. The orgnic layers were wahed with water and 10% sodium chloride solution concentrated in vacuo and dissolved in THF (10V) and water (5V). The mixture was cooled to 0° C. and trifluoroacetic acid (5V) was slowly added over a period of 30-60 min. The reaction was warmed to 30° C. and stirred for 14 to 18 hours. In another vessel 6.3 Eq. sodium bicarbonate was dissolved in 90V water was cooled to 10° C. The reaction mass was slowly quenched into the cooled sodium bicarbonate solution at 10° C. over a period of 60-120 min. The mixture was extracted with ethyl acetate and the combined organics were washed with water, 7% sodium bicarbonate solution and 10% sodium chloride solution. Following purification, the reaction provided NUC-7738 as a mixture of diastereoisomers.

The invention claimed is:

1. A process for the preparation of NUC-7738 (I)

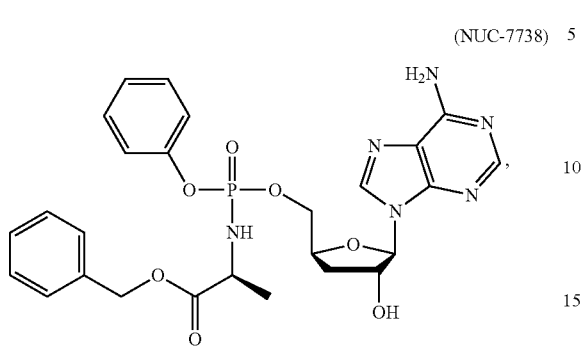

(NUC-7738)

the process comprising steps b), c), d), e) and f):

b) treating a compound of formula (VI) with a hydride reducing agent to provide a compound of formula (V)

(VI)

(V)

c) introducing the protecting group $P^2$ onto the 2' hydroxy group of a compound of formula (V) to provide a compound of formula (II)

(II)

d) removing the protecting group $P^1$ from a compound of formula (II) to provide 2'-protected Cordycepin (I)

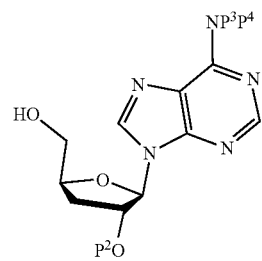

(I)

wherein $P^1$ and $P^2$ are silyl protecting groups and $P^3$ and $P^4$ are each independently selected from H and a protecting group;

e) converting the compound of formula (I) into a compound of formula (IV)

(IV)

(IV); and f) removing protecting group $P^2$ and, where $P^3$ and $P^4$ are protecting groups, removing $P^3$ and $P^4$ to provide NUC-7738;

wherein the overall yield of steps b), c), and d) is 70%-100%.

2. The process of claim 1, wherein the process further comprises step a):

a) introducing the protecting group $P^1$ onto the 5' hydroxy group of a compound of formula (VII) to provide a compound of formula (VI)

(VII)

3. The process of claim 1, wherein $P^3$ and $P^4$ are each H.
4. The process of claim 1, wherein step d) is achieved with trifluoroacetic acid (TFA).
5. The process of claim 4, wherein step d) is achieved in a mixture of acetonitrile and water.
6. The process of claim 4, wherein step d) is carried out at a temperature between 0° C. and 20° C.
7. The process of claim 1, wherein the NUC-7738 is formed as a mixture of diastereoisomers.

8. The process of claim 7, wherein step e) comprises: reacting the compound of formula (I) with a compound of formula (III) in the presence of a base (B1) to provide a compound of formula (IV); wherein the compound of formula (III) is:
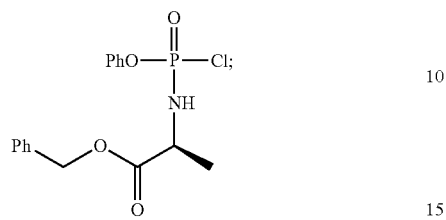
and wherein B1 is a nitrogen base, an organometallic base or a metal hydride base.
* * * * *